US012714739B2

(12) United States Patent
Diener et al.

(10) Patent No.: US 12,714,739 B2
(45) **Date of Patent: *Aug. 25, 2026**

(54) METHODS OF TREATING HIV-HAART INDUCED PARTIAL LIPODYSTROPHY WITH FGF21 PROTEIN VARIANT FC FUSION PROTEINS

(71) Applicant: Novartis AG, Basel (CH)

(72) Inventors: John Louis Diener, Cambridge, MA (US); Jiaping Gao, Ashland, MA (US); Rick Jerome Schiebinger, Cambridge, MA (US)

(73) Assignee: Novartis AG, Basel (CH)

( * ) Notice: Subject to any disclaimer, the term of this patent is extended or adjusted under 35 U.S.C. 154(b) by 240 days.

This patent is subject to a terminal disclaimer.

(21) Appl. No.: 18/609,420

(22) Filed: Mar. 19, 2024

(65) Prior Publication Data

US 2024/0293508 A1 Sep. 5, 2024

Related U.S. Application Data

(63) Continuation of application No. 16/407,813, filed on May 9, 2019, now Pat. No. 11,963,999, which is a continuation of application No. 15/124,877, filed as application No. PCT/US2015/019362 on Mar. 9, 2015, now abandoned.

(60) Provisional application No. 61/950,960, filed on Mar. 11, 2014.

(51) Int. Cl.
*A61K 38/18* (2006.01)
*C07K 14/50* (2006.01)

(52) U.S. Cl.
CPC .......... *A61K 38/1825* (2013.01); *C07K 14/50* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 2012/0129766 | A1 | 5/2012 | Boettcher et al. |
| 2013/0079500 | A1 | 3/2013 | Boettcher et al. |
| 2013/0085098 | A1 | 4/2013 | Dickinson et al. |
| 2013/0129724 | A1 | 5/2013 | Boettcher et al. |
| 2013/0129725 | A1 | 5/2013 | Fachíni et al. |
| 2014/0142023 | A1 | 5/2014 | Sommerfeld et al. |

FOREIGN PATENT DOCUMENTS

| | | |
|---|---|---|
| WO | 2001/018172 | 3/2001 |
| WO | 2004003179 | 1/2004 |
| WO | 2004110472 | 12/2004 |
| WO | 2005/000892 | 1/2005 |
| WO | 2005/061712 | 7/2005 |
| WO | 2005/113606 | 12/2005 |
| WO | 2006/050247 | 5/2006 |
| WO | 2008121563 | 10/2008 |
| WO | 2009/020802 | 2/2009 |
| WO | 2009/117622 | 9/2009 |
| WO | 2009/149171 | 12/2009 |
| WO | 2010/042747 | 4/2010 |
| WO | 2010/084169 | 7/2010 |
| WO | 2010/129503 | 11/2010 |
| WO | 2010/129600 | 11/2010 |
| WO | 2011/047267 | 4/2011 |
| WO | 2011/071783 | 6/2011 |
| WO | 2011/089170 | 7/2011 |
| WO | 2011/089203 | 7/2011 |
| WO | 2011130417 | 10/2011 |
| WO | 2011/154349 | 12/2011 |
| WO | 2012/010553 | 1/2012 |
| WO | 2012/040518 | 3/2012 |
| WO | 2012/059873 | 5/2012 |
| WO | 2012066075 | 5/2012 |
| WO | 2012/177481 | 12/2012 |
| WO | 2013/006486 | 1/2013 |
| WO | 2013/010780 | 1/2013 |
| WO | 2013033452 | 3/2013 |
| WO | 2013049234 | 4/2013 |
| WO | 2013049247 | 4/2013 |
| WO | 2013/188181 | 12/2013 |
| WO | 2014/031420 | 2/2014 |
| WO | 2014/037373 | 3/2014 |
| WO | 2014085365 | 6/2014 |

(Continued)

OTHER PUBLICATIONS

Miehle, et al., "Serum concentrations of fibroblast growth factor 21 are elevated in patients with congenital or acquired lipodystrophy," Cytokine, vol. 83, pp. 239-244, 2016.
Joy et al., "Dietary Fat Intake and Relationship to Serum Lipid Levels Among HIV-Infected Subjects with Metabolic Abnormalities in the Era of HAART," available in PMC Apr. 11, 2015, published in final edited form as: AIDS. 21(12): 1591-1600 (Jul. 2007) (22 pages).
Singhania et al., (HIVAIDS Research and Palliative Care 3: 135-143 2011).
Harald Staiger et al., "Fibroblast Growth Factor 21-Metabolic Role in Mice and Men", Endocrine Reviews, US, (Jul. 28, 2017), vol. 38, No. 5, doi:10.1210/er.2017-00016, ISSN 0163-769X, pp. 468-488.
Murielle M. Véniant et al, "Long-Acting FGF21 Has Enhanced Efficacy in Diet-Induced Obese Mice and in Obese Rhesus Monkeys", Endocrinology, US, (Sep. 1, 2012), vol. 153, No. 9, doi:10.1210/en.2012-1211, ISSN 0013-7227, pp. 4192-4203.

(Continued)

*Primary Examiner* — Christine J Saoud
(74) *Attorney, Agent, or Firm* — Morgan, Lewis & Bockius LLP

(57) ABSTRACT

The invention relates to the identification of new therapeutic methods for the FGF21 polypeptide or protein, or mutants, variants, and fusions thereof, for instance, in treating metabolic diseases associated defects in insulin signaling (e.g. insulin receptor mutation disorders (INSR disorders) and/or autoimmune insulin receptor disorders (Type B insulin Resistance)), defects in insulin production such as type 1 diabetes mellitus, mixed dyslipidemia, nonalcoholic fatty liver disease (NAFLD), and other metabolic disorders, and various lipodystrophies such as HIV-HAART induced partial-lipodystrophy, and in reducing the mortality and morbidity of critically ill patients.

20 Claims, 16 Drawing Sheets

Specification includes a Sequence Listing.

(56) References Cited

FOREIGN PATENT DOCUMENTS

| | | |
|---|---|---|
| WO | 2014/105939 | 7/2014 |
| WO | 2014/149699 | 9/2014 |
| WO | 2015138278 A1 | 9/2015 |
| WO | 2015/148708 | 10/2015 |
| WO | 2015/183890 | 12/2015 |
| WO | 2015/195509 | 12/2015 |
| WO | 2016/048999 | 4/2016 |
| WO | 2016/065326 | 4/2016 |

OTHER PUBLICATIONS

Hecht, R. et al., 'Rationale-Based Engineering of a Potent Long-Acting FGF21 Analog for the Treatment of Type 2 Diabetes', PLOS ONE, Nov. 2012, vol. 7, No. 11, e49345.

Weng Y. et al., 'Glyco-engineered Long Acting FGF21 Variant with Optimal Pharmaceutical and Pharmacokinetic Properties to Enable Weekly to Twice Monthly Subcutaneous Dosing', Scientific Reports, Mar. 9, 2018, vol. 8, No. 4241, pp. 1-15.

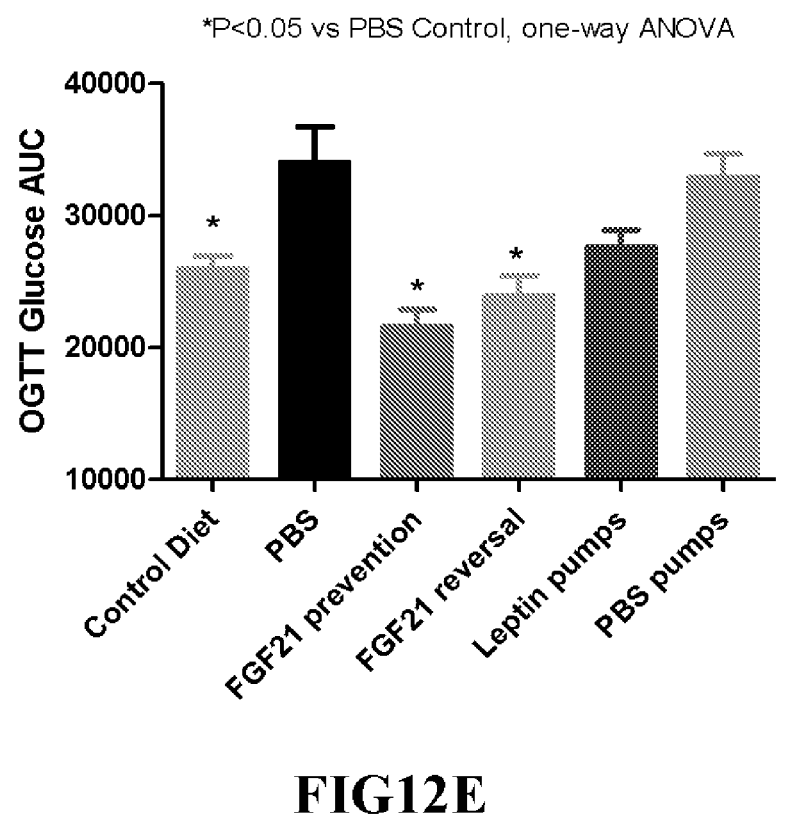

*P<0.05 vs PBS Control, one-way ANOVA

OGTT Glucose AUC 40000
30000
20000
10000

Control Diet
PBS
FGF21 prevention
FGF21 reversal
Leptin pumps
PBS pumps

FIG12E

METHODS OF TREATING HIV-HAART INDUCED PARTIAL LIPODYSTROPHY WITH FGF21 PROTEIN VARIANT FC FUSION PROTEINS

RELATED APPLICATIONS

This application is a continuation of U.S. patent application Ser. No. 16/407,813 (now U.S. Pat. No. 11,963,999), filed May 9, 2019, which is a continuation of U.S. patent application Ser. No. 15/124,877, filed on Sep. 9, 2016, which is a national stage entry of PCT/US2015/019362, filed on Mar. 9, 2015, which claims the benefit of and priority to U.S. Provisional Patent Application No. 61/950,960 filed on Mar. 11, 2014. The contents of each of the foregoing applications are hereby incorporated by reference in their entireties.

SEQUENCE LISTING

This present application is filed with a Sequence Listing. The Sequence Listing is provided as an XML file entitled "BPH-002C2_Sequence_Listing.xml" created on Mar. 18, 2024, which is 13,086 bytes in size. The information in the electronic format of the Sequence Listing is incorporated herein by reference in its entirety.

FIELD OF THE INVENTION

The present invention relates to methods of treating metabolic diseases associated with insulin resistance, specifically insulin receptor disorders (INSR disorders, or IR disorders) including those resulting from mutations in the insulin receptor (e.g., Type A insulin resistance, Rabson Mendenhall and Donohue Syndromes) and autoimmune insulin resistance (aka Type B insulin resistance); insulin resistance and associated mixed dyslipidemias caused by familial partial lipodystrophy, acquired partial lipodystrophy, and HIV/HAART-induced partial lipodystrophy disorders, and in reducing the mortality and morbidity of these patients. The present invention also relates to methods of treating patients with defects in insulin production, such as those suffering from type 1 diabetes mellitus.

BACKGROUND OF THE INVENTION

The fibroblast growth factor (FGF) family is characterized by 22 genetically distinct, homologous ligands, which are grouped into seven subfamilies. According to the published literature, the FGF family now consists of at least twenty-three members, FGF-1 to FGF-23 (Reuss et al. (2003) Cell Tissue Res. 313:139-157).

FGF-21 was isolated from mouse embryos and is closest to FGF-19 and FGF-23. This FGF subfamily regulates diverse physiological processes uncommon to classical FGFs, namely energy and bile acid homeostasis, glucose and lipid metabolism and phosphate as well as vitamin D homeostasis. Moreover, unlike classical FGFs, this subfamily acts in an endocrine fashion. (Moore, D. D. (2007) Science 316, 1436-8). Fibroblast growth factor 21 (FGF21) has been reported to be preferentially expressed in the liver (Nishimura et al., Biochimica et Biophysica Acta, 1492:203-206, (2000); patent publication WO01/36640; and patent publication WO01/18172) and described as a treatment for ischemic vascular disease, wound healing, and diseases associated with loss of pulmonary, bronchia or alveolar cell function and numerous other disorders.

FGF21 has been identified as a potent metabolic regulator. Systemic administration of FGF21 to rodents and rhesus monkeys with diet-induced or genetic obesity and diabetes exerts strong anti-hyperglycemic and triglyceride-lowering effects, and reduction of body weight. (Coskun, T, et al. (2008) Endocrinology 149:6018-6027; Kharitonenkov, A, et al. (2005) Journal of Clinical Investigation 115:1627-1635; Kharitonenkov, A, et al. (2007) Endocrinology 148:774-781; Xu, J, et al. (2009) Diabetes 58:250-259). FGF21 is a 209 amino acid polypeptide containing a 28 amino acid leader sequence. Human FGF21 has about 79% amino acid identity to mouse FGF21 and about 80% amino acid identity to rat FGF21.

Although FGF-21 activates FGF receptors and downstream signaling molecules, including FRS2a and ERK, direct interaction of FGFRs alone and FGF-21 has not been detected. Furthermore, many cell types do not respond to FGF-21, even though they express multiple FGFR isoforms. All of these data suggest that a cofactor must mediate FGF-21 signaling through FGFRs. Recent studies have identified ß-klotho, which is highly expressed in liver, adipocytes and in pancreas, as a determinant of the cellular response to FGF-21 (Kurosu, H. et al. (2007) J Biol Chem 282, 26687-95). ß-klotho preferentially binds to FGFR1c, FGFr2c, FGFR3c, and FGFR4. The ß-klotho-FGFR complex, but not FGFR alone, binds to FGF-21 in vitro (Kharitonenkov, A. et al. (2008) J Cell Physiol 215, 1-7). A similar mechanism has been identified in the FGF-23-klotho-FGFR system (Urakawa, I. et al. (2006) Nature 444, 770-4).

The bioactivity of FGF-21 was first identified in a mouse 3T3-L1 adipocyte glucose uptake assay (Kharitonenkov, A. et al. (2005) J Clin Invest 115, 1627-35). Subsequently, FGF-21 was shown to induce insulin-independent glucose uptake and GLUT1 expression. FGF-21 has also been shown to ameliorate hyperglycemia in a range of diabetic rodent models. In addition, transgenic mice over-expressing FGF-21 were found to be resistant to diet-induced metabolic abnormalities, including decreased body weight and fat mass, and enhancements in insulin sensitivity (Badman, M. K. et al. (2007) Cell Metab 5, 426-37). Administration of FGF-21 to diabetic non-human primates caused a decline in fasting plasma glucose, triglycerides, insulin and glucagon levels, and led to significant improvements in lipoprotein profiles including a nearly 80% increase in HDL cholesterol (Kharitonenkov, A. et al. (2007) Endocrinology 148, 774-81). Importantly, hypoglycemia was not observed at any point during this NHP study. Moreover, recent studies identified FGF-21 as an important endocrine hormone that helps to control adaptation to the fasting state. This provides a previously missing link, downstream of PPARa, by which the liver communicates with the rest of the body in regulating the biology of energy homeostasis.

The FGF21 polypeptide and protein, as well as variants and mutations thereof, have been evaluated for their metabolic effects on obesity and type 2 diabetes (T2D). The effect of FGF21 on insulin receptor mutation disorders (INSR disorders) and various metabolic conditions associated with lipodystrophy, however, has not been demonstrated. In this application, the effect of FGF21 on T1D, insulin receptor mutation or autoimmune disorders (INSR disorders) and HIV/HAART (Highly Active Anti-Retroviral Therapy (used to treat patients with HIV infection)) induced partial lipodystrophy is described, and the methods of the present invention are useful for the treatment of said metabolic diseases in addition to the known diseases associated with T2DM and insulin resistance.

SUMMARY OF THE INVENTION

The invention relates to the identification of new therapeutic functions for fibroblast growth factor 21 (FGF21) proteins and polypeptides, including variants and mutations thereof, and pharmaceutical compositions comprising the same, i.e., as agents to treat metabolic diseases associated with insulin resistance, including metabolic conditions associated with insulin receptor (INSR) mutations.

In some embodiments, the methods of the invention comprise the wild type FGF21 protein, e.g., having NCBI reference sequence number NP 061986.1, and encoded by the polynucleotide sequence which has NCBI reference sequence number NM 019113.2, and found in such issued patents as, e.g., U.S. Pat. No. 6,716,626B1, assigned to Chiron Corporation.

In some embodiments, the methods of the invention comprise variants of the FGF21 protein sequence, e.g., biologically active FGF21 variants, and can include truncated versions of the FGF21 protein (in which residues from the C- and/or N-terminal regions have been eliminated, thereby shortening/truncating the protein), as well as variants with one or more point substitutions and/or site-specific incorporation of amino acids at positions of interest (e.g., with conservative amino acid residues, with non-conservative residues, or with non-natural amino acid residues such as pyrrolysine).

Representative examples of said variants are described, e.g., in PCT Publication WO2012/066075 (filed 24 May 2012 by Novartis AG). A preferred embodiment is described as "Variant 76," "FGF21 V76," "V76," or the like in PCT publication WO2012/066075 and herein, which is a genetically engineered FGF21 variant with 177 amino acid residues, including 9 point mutations. Another preferred embodiment is described as "Variant 101," "FGF21 (v101)," "V101," or the like in PCT publication WO2013/049247 and herein, which is an Fc fusion protein linked by a two amino acid liker to a genetically engineered FGF21 variant with 9 point mutations. Preferred embodiments can be found in the following table:

TABLE 1

FGF21 Variant Fc fusion proteins

| SEQ ID NO: | Sequence | Name* |
|---|---|---|
| 1 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGSD SSPLLQFGGQ<br>VRQRYLYTDD AQQTEAHLEI REDGTVGGAA DQSPESLLQL<br>KALKPGVIQI LGVKTSRFLC QRPDGALYGS LHFDPEACSF<br>RELLLEDGYN VYQSEAHGLP LHLPGNKSPH RDPAPRGPAR<br>FLPLPGLPPA LPEPPGILAP QPPDVGSSDP LSMVGPSQGR<br>SPSYAS | Full Length N-term Fc-Fusion with 2 AA Linker (GS) and WT FGF21 |
| 2 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGGG GSGGGGSGGG<br>GSDSSPLLQF GGQVRQRYLY TDDAQQTEAH LEIREDGTVG<br>GAADQSPESL LQLKALKPGV IQILGVKTSR FLCQRPDGAL<br>YGSLHFDPEA CSFRELLLED GYNVYQSEAH GLPLHLPGNK<br>SPHRDPAPRG RARFLPLPGL PPALPEPPGI LAPQPPDVGS<br>SDPLSMVGPS QGRSPSYAS | Full Length N-term Fc-Fusion with 15 AA Linker (GGGGS ×X 3) between Fc and WT FGF21 |
| 3 | DSSPLLQFGG QVRQRYLYTD DAQETEAHLE IREDGTVGGA<br>AHQSPESLLE LKALKPGVIQ ILGVKTSRFL CQKPDGALYG<br>SLHFDPEACS FRELLLEDGY NVYQSEAHGL PLHLPGNRSP<br>HCDPAPQGPA RFLPLPGLPP ALPEPPGILA PQPPDVGSSD<br>PLAMVGPSQG RSPSYAS | Variant #76 = Protein with 9 total mutations relative to wild-type FGF21 (as in WO01/018172) |
| 4 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGSD SSPLLQFGGQ<br>VRQRYLYTDD ACQTEAHLEI REDGTVGGAA DQSPESLLQL<br>KALKPGVIQI LGVKTSRFLC QRPDGTLYGS LHFDPEACSF<br>RELLLEDGYN VYQSEAHGLP LHLPCNRSPH RDPASRGPAR<br>FLPLPGLPPA LPEPPGILAP QPPDVGSSDP LAMVGGSQAR<br>SPSYAS | Variant # 101 = N-term Fc Fusion with the 2 AA linker (GS) between Fc and FGF21 = (Q55C, A109T, G148C, K150R, P158S, S195A, P199G, G202A) |
| 5 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE | Variant # 103 = N-term Fc Fusion with the 2 AA |

TABLE 1-continued

FGF21 Variant Fc fusion proteins

| SEQ ID NO: | Sequence | Name* |
| --- | --- | --- |
| | WESNGQPENN YKTTPPVLDS DGSFFLYSKL TVDKSRWQQG<br>NVFSCSVMHE ALHNHYTQKS LSLSPGKGSD SSPLLQFGGQ<br>VRQRYLYTDD ACQTEAHLEI REDGTVGGAA DQSPESLLQL<br>KALKPGVIQI LGVKTSRFLC QKPDGALYGS LHFDPEACSF<br>RELLLEDGYN VYQSEAHGLP LHLPCNRSPH RDPASRGPAR<br>FLPLPGLPPA LPEPPGILAP QPPDVGSSDP LAMVGGSQAR<br>SPSYAS | linker (GS)<br>between Fc and<br>FGF21 = (Q55C,<br>A109T, G148C,<br>K150R, P158S,<br>S195A, P199G,<br>G202A) |
| 6 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGSD SSPLLQFGGQ<br>VRQRYLYTDD ACQTEAHLEI REDGTVGGAA HQSPESLLEL<br>KALKPGVIQI LGVKTSRFLC QKPDGALYGS LHFDPEACSF<br>RELLLEDGYN VYQSEAHGLP LHLPCNRSPH RDPAPQGPAR<br>FLPLPGLPPA LPEPPGILAP QPPDVGSSDP LAMVGPSQGR<br>SPSYAS | Variant # 104 =<br>N-term Fc<br>Fusion with<br>the 2 AA<br>linker (GS) =<br>(Q55C, D74H,<br>Q82E, R105K,<br>G148C, K150R,<br>R159Q, P174L,<br>S195A) |
| 7 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGGG GSGGGGSGGG<br>GSDSSPLLQF GGQVRQRYLY TDDACQTEAH LEIREDGTVG<br>GAAHQSPESL LELKALKPGV IQILGVKTSR FLCQKPDGAL<br>YGSLHFDPEA CSFRELLLED GYNVYQSEAH GLPLHLPCNR<br>SPHRDPAPQG RARFLPLPGL PPALPEPPGI LAPQPPDVGS<br>SDPLAMVGPS QGRSPSYAS | Variant # 183 =<br>V104 with 15<br>AA Linker<br>(GGGGS × 3)<br>between Fc and<br>FGF21 =<br>(Q55C, D74H,<br>Q82E, R105K,<br>G148C, K150R,<br>R159Q, P174L,<br>S195A) |
| 8 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGGG GSGGGGSGGG<br>GSDSSPLLQF GGQVRQRYLY TDDACQTEAH LEIREDGTVG<br>GAADQSPESL LQLKALKPGV IQILGVKTSR FLCQKPDGAL<br>YGSLHFDPEA CSFRELLLED GYNVYQSEAH GLPLHLPCNR<br>SPHRDPASRG RARFLPLPGL PPALPEPPGI LAPQPPDVGS<br>SDPLAMVGGS QARSPSYAS | Variant #188 =<br>V103 with 15<br>AA Linker<br>(GGGGS × 3)<br>between Fc and<br>FGF21 = (Q55C,<br>R105K, G148C,<br>K150R, P158S,<br>S195A, P199G,<br>G202A) |
| 9 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK<br>GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPGKGGG GSGGGGSGGG<br>GSDSSPLLQF GGQVRQRYLY TDDACQTEAH LEIREDGTVG<br>GAADQSPESL LQLKALKPGV IQILGVKTSR FLCQRPDGTL<br>YGSLHFDPEA CSFRELLLED GYNVYQSEAH GLPLHLPCNR<br>SPHRDPASRG RARFLPLPGL PPALPEPPGI LAPQPPDVGS<br>SDPLAMVGGS QARSPSYAS | Variant #204 =<br>V101 with 15<br>AA Linker<br>(GGGGS × 3)<br>between Fc and<br>FGF21 = (Q55C,<br>A109T, G148C,<br>K150R, P158S,<br>S195A, P199G,<br>G202A) |

*Note that the FGF21 wild-type sequence in this label refers to NCBI reference sequence number NP_061986.1 unless otherwise specified.

Said modifications of FGF21 used in the methods of the present invention are designed to enhance the biological properties of the variants relative to the wild-type FGF21 protein, as well as, in some cases, serving as points of attachment for, e.g., labels and protein half-life extension agents, and for purposes of affixing said variants to the surface of a solid support.

In various embodiments, said polypeptide and protein variants disclosed herein can comprise (a) an amino-terminal truncation of no more than 8 amino acid residues, wherein the polypeptide is capable of lowering blood glucose in a mammal; (b) a carboxyl-terminal truncation of no more than 12 amino acid residues, wherein the polypeptide is capable of lowering blood glucose in a mammal; or (c) an amino-terminal truncation of no more than 8 amino acid residues and a carboxyl-terminal truncation of no more than 12 amino acid residues, wherein the polypeptide is capable of lowering blood glucose in a mammal.

In still other embodiments, the methods of the invention comprise variants of the FGF21 protein sequence, such as those described, e.g., in the following:

- US issued patents U.S. Pat. Nos. 7,491,697; 8,541,369; 8,012,931; 8,383,365;
- US and PCT published patent applications US2011/0195895; US2012/0052069; US2010/0216715; US2009/0118190; US2012/0264683; WO10/084169; WO10/142665; US2008/0176790; WO11/089203; WO11/020319; WO12/062078; US2010/0285131; WO10/042747; and US2011/0135657;

as well as any related applications, issued patents, and family members of the above, both in the US and in the rest of the world.

In still other embodiments, the methods of the invention comprise variants of the FGF21 protein sequence in which disulfide bonds have been engineered, e.g., by the addition of cysteine residues. Said variants can be found, e.g., in PCT Publication WO12/066075, as well as in any of the variants with engineered disulfide bonds listed in the positions above.

In some embodiments, the methods of the invention comprise PEGylated or otherwise half-life extended FGF21 polypeptides or proteins, e.g., wild type FGF21, or mutants or variants thereof.

In some embodiments, the methods of the invention comprise polypeptide and protein variants covalently linked to one or more polymers, such as polyethylene glycol (PEG) or polysialic acid, whether at the position of site-specific amino acid modifications made relative to the wild-type FGF21, or at the position of amino acids commonly shared with the wild-type FGF21.

In some embodiments, the methods of the invention comprise FGF21 fusion proteins, such as Fc fusions. Said fusions can comprise wild type FGF21 or mutants or variants thereof. In some embodiments, the methods of the present invention comprise polypeptides which can be fused to a heterologous amino acid sequence, optionally via a linker, such as GS or GGGGSGGGGSGGGGS (SEQ ID NO:10). The heterologous amino acid sequence can be an IgG constant domain or fragment thereof (e.g., the Fc region), Human Serum Albumin (HSA), or albumin-binding polypeptides. Such methods can comprise multimers of said fusion polypeptides. In some embodiments, the methods of the present invention comprise fusion proteins in which the heterologous amino acid sequence (e.g., HSA, Fc, etc.) is fused to the amino-terminal of the FGF21 protein or mutants or variants as described; in other embodiments, the fusion occurs at the carboxyl-terminal of the FGF21 protein or mutants or variants.

The invention also provides methods of treatment which comprise pharmaceutical compositions comprising the polypeptide and protein variants disclosed herein and a pharmaceutically acceptable formulation agent. Such pharmaceutical compositions can be used in a method for treating a metabolic disorder, and the method comprises administering to a human patient in need thereof a pharmaceutical composition of the invention. Non-limiting examples of metabolic disorders that can be treated include type 1 diabetes mellitus and INSR mutation disorders.

These and other aspects of the invention will be elucidated in the following detailed description of the invention.

BRIEF DESCRIPTION OF THE DRAWINGS

FIG. 12E shows that under the same conditions, FGF21 (v101), administered in either prevention or treatment mode, but not leptin in treatment mode, can reverse said induced glucose intolerance, as measured using an OGTT.

DETAILED DESCRIPTION OF THE INVENTION

Figure 1A:
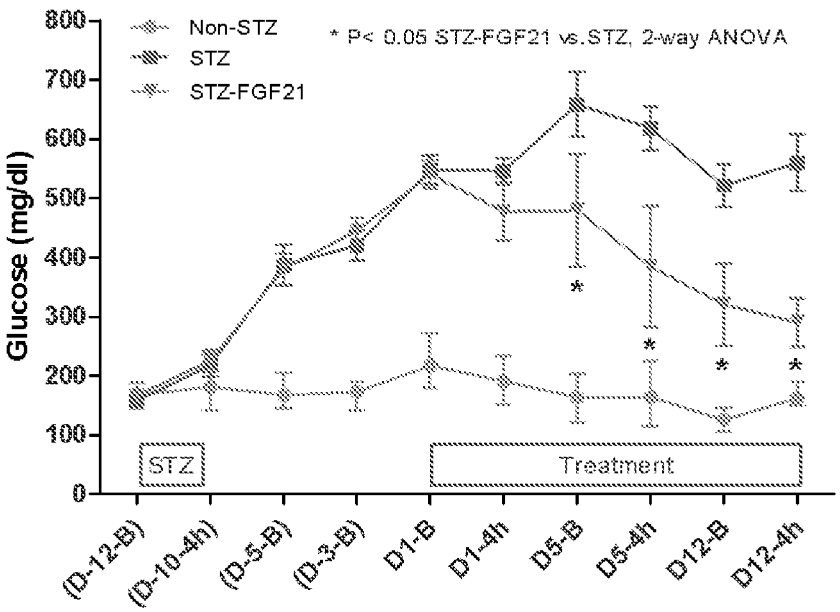
FIGS. 1A and 1B are graphical representations showing a change in glucose levels when STZ mice are administered wild type FGF21 (FIG. 1A) and Variant 76 (Cmpd-A) (FIG. 1B). [STZ is the beta cell toxin streptozotocin.] Wild type FGF21 (3 mg/kg, daily dose) decreased glucose in STZ mice from day 5 (D5). Variant 76 (referred to as Cmpd-A)(1 or 3 mg/kg, 2 doses/week) decreased glucose in STZ mice from day 2 (D2) with 3 mg/kg dose and day 11 (D11) with 1 mg/kg dose.

The methods of the present invention are based on the discovery of an improved therapeutic treatment for subjects afflicted with Type 1 diabetes and metabolic diseases associated with insulin resistance, e.g., disorders associated with insulin receptor (IR) mutations or lipodystrophies.

Multiple inactivating mutations of the INSR have been described with varying phenotypes. Patients typically present with severe resistance to the action of insulin which advances to hyperglycemia at the time of puberty. The current standard of care is treatment with very high doses of insulin when subjects become hyperglycemic, which typically is inadequate in controlling hyperglycemia. Treatments to date have been met with limited success.

FGF21 polypeptides and proteins, as well as variants, fusions, and mutations thereof, have long been recognized for their metabolic effects on obesity and type 2 diabetes (T2D). The effect of FGF21 on type 1 diabetes (T1D), insulin receptor mutation disorders, and lipodystrophies, however, has not been demonstrated until the present methods of the invention. In this application, the effect of FGF21 on T1D and insulin receptor mutation disorders and lipodystrophies is described, and the claimed methods of the present invention can be employed for the treatment of said metabolic diseases associated with insulin resistance, e.g., Type 1 DM, insulin receptor disorders (INSR disorders) including Type B insulin resistance and HIV/HAART-induced partial lipodystrophy.

As described further herein, high dose streptozotocin (STZ)-treated mice are commonly used as a rodent model of type 1 diabetes (T1D), which exhibit hyperglycemia, insulinopenia, excessive lipid utilization and ketogenesis, as well as hyperphagia. [STZ is a beta cell toxin, administered to destroy beta cells, e.g., in the creation of mouse models with T1D-like symptoms.] Treatment with either daily dose of wild type FGF21 or two doses a week of half-life-extended FGF21 was efficacious on improving overall disease condition in STZ mice, leading to a reduction in hyperglycemia, excessive food consumption and accumulation of ketone bodies, and an increase in utilization of carbohydrate and energy expenditure.

Treatment with Variant 76 did not restore insulin secretion in the STZ treated animals. Despite the early observation that FGF21 could induce glucose uptake in adipocytes in the absence of insulin, we are the first to propose and these STZ data are the first to establish this effect in vivo and to demonstrate that FGF21 treatment can work in the setting of T1D. Therefore, the administration of wild type FGF21 polypeptide and protein, or of variants, fusions, or mutants, thereof, can provide therapeutic value in treating T1D.

Because of the demonstrated effect of FGF21 in the STZ model in the absence of any increase in insulin secretion we propose that an FGF21 analog could be used to treat diseases of impaired insulin signaling caused by dysfunction of INSR itself (either by mutation in INSR or by neutralizing autoantibodies to INSR). However, since, INSR KO mice are not viable and die postnatally, an equivalent animal model to the human condition does not currently exist. Furthermore tissue specific KO of insulin receptor in mice fails to fully recapitulate the various disease states seen in humans with either mutation in INSR or autoantibodies to INSR. Therefore we used an anti-human INSR antibody to demonstrate that under conditions where glucose uptake by insulin was completely blocked by the Ab (10 nM Ab), FGF21 could still promote significant glucose uptake in these cells. These data support the novel use of an FGF21 therapy in patients with defects in INSR caused either by mutation or by anti-insulin receptor antibodies.

It has been long established that an FGF21 analog can be used to treat hyperglycemia, insulin resistance, obesity, and dyslipidemia in diabetic leptin deficient ob/ob mice (Kharitonenkov, A, et al. (2005) Journal of Clinical Investigation 115). A common property of these mice is significant accumulation of liver fat. Liver fat in these animals is rapidly and dose dependently reduced with FGF21 treatment. Significant increase in liver fat is also associated with the types of insulin resistance and associated mixed dyslipidemias caused by congenital generalized or familial partial lipodystrophy, acquired generalized or acquired partial lipodystrophy, HIV/HAART-induced partial lipodystrophy and/or lipohypertrophy, and other lipid metabolism dysfunctions caused by HAART. Here we demonstrate the novel method of treatment of two chemically induced lipodystrophies (c10-t12 linoleic acid and HIV protease inhibitor Ritonavir) using an FGF21 analog. In these examples the exact mechanism of induction of lipodystrophy is different and therefore these data should extend to the treatment of any lipodystrophy associated with loss of peripheral fat and accumulation of liver fat that leads to insulin resistance and dyslipidemia using an FGF21 analog.

The methods of the present invention comprise wild type FGF21 polypeptide and proteins, fusions, and variants and mutants thereof. The FGF21 wild-type sequence has NCBI reference sequence number NP_061986.1, and is encoded by the polynucleotide sequence which has NCBI reference sequence number NM_019113.2, and can be found in such issued patents as, e.g., U.S. Pat. No. 6,716,626B1, assigned to Chiron Corporation.

The mature FGF21 sequence lacks a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art.

One skilled in the art of expression of proteins will recognize that methionine or methionine-arginine sequence can be introduced at the N-terminus of any of the FGF21 protein variants, for expression in *E. coli*, and are contemplated within the context of the methods of this invention.

The terms "FGF21 protein variant," "human FGF21 variant," "FGF21 polypeptide or protein variant," "variant," "FGF21 mutant," or any like terms, are defined as comprising human FGF21 in which a naturally occurring (i.e., wild-type) FGF21 amino acid sequence has been modified, e.g., in which at least one amino acid of the wild-type protein has been substituted by another amino acid, and/or removed. Additionally, the variants may include N- and/or C-terminal truncations relative to the wild-type FGF21 protein. Generally speaking, a variant possesses some modified property, structural or functional, of the wild-type protein. For example, the variant may have enhanced or improved physical stability in concentrated solutions (e.g., less hydrophobic mediated aggregation), enhanced or improved plasma stability when incubated with blood plasma or enhanced or improved bioactivity while maintaining a favorable bioactivity profile.

Acceptable amino acid substitutions and modifications which constitute differences between the FGF21 polypeptide and protein variants and mutants of the methods of the invention and wild-type FGF21 include, but are not limited to, one or more amino acid substitutions, including substitutions with non-naturally occurring amino acid analogs, and truncations. Thus, FGF21 protein variants include, but are not limited to, site-directed FGF21 mutants, truncated FGF21 polypeptides, proteolysis-resistant FGF21 mutants, aggregation-reducing FGF21 mutants, FGF21 combination mutants, and FGF21 fusion proteins, as described herein.

The variant may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. Accordingly, variants with enhanced pharmaceutical stability relative to wild-type FGF21, have improved physical stability in concentrated solutions under both physiological and preserved pharmaceutical formulation conditions, while maintaining biological potency. By way of non-limiting example, the variants of the invention may be more resistant to proteolysis and enzymatic degradation; may have improved stability; and may be less likely to aggregate, than their wild-type counterparts. As used herein, these terms are not mutually exclusive or limiting, it being entirely possible that a given variant has one or more modified properties of the wild-type protein.

DEFINITIONS

Various definitions are used throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "FGF21" refers to a member of the fibroblast growth factor (FGF) protein family and has the GenBank Accession No. NP_061986.1 (the corresponding polynucleotide sequence of which has NCBI reference sequence number NM_019113.2), and can be found in such issued patents as, e.g., U.S. Pat. No. 6,716,626B1, assigned to Chiron Corporation.

As used herein, the term "FGF21 receptor" refers to a receptor for FGF21 (Kharitonenkov, A, et al. (2008) Journal of Cellular Physiology 215:1-7; Kurosu, H, et al. (2007) JBC 282:26687-26695; Ogawa, Y, et al. (2007) PNAS 104:7432-7437).

The term "FGF21 polypeptide" refers to a naturally-occurring polypeptide expressed in humans. For purposes of this disclosure, the term "FGF21 polypeptide" can be used interchangeably to refer to any full-length FGF21 polypeptide, which consists of 209 amino acid residues; any mature form of the polypeptide, which consists of 181 amino acid residues, and in which the 28 amino acid residues at the amino-terminal end of the full-length FGF21 polypeptide (i.e., which constitute the signal peptide) have been removed; and variants thereof.

The term "isolated nucleic acid molecule" refers to a nucleic acid molecule of the present invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The term "isolated polypeptide" refers to a polypeptide (e.g., a FGF21 polypeptide or variant FGF21 polypeptide provided herein) that has been separated from at least about 50 percent of polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (PYL), and pyrroline-carboxy-lysine (PCL).

Pyrrolysine (PYL) is an amino acid naturally found within methylamine methyltransferases of methanogenic archaea of the family Methanosarcina. Pyrrolysine is a lysine analogue co-translationally incorporated at in-frame UAG codons in the respective mRNA, and it is considered the 22nd natural amino acid.

As described at least in PCT patent publication WO2010/48582 (applicant IRM, LLC), attempts to biosynthesize pyrrolysine (PYL) in *E. coli* resulted in the formation of a "demethylated pyrrolysine," referred to herein as pyrroline-carboxy-lysine, or PCL. "PCL," as used herein, refers to either PCL-A or PCL-B.

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) FGF21 protein sequence or the sequences of the FGF21 variants of the present invention. These include, but are not limited to, modified amino acids and/or amino acid analogues that are not one of the 20 naturally occurring amino acids, selenocysteine, pyrrolysine (PYL), or pyrroline-carboxy-lysine (PCL). Such non-natural amino acid residues can be introduced by substitution of naturally occurring amino acids, and/or by insertion of non-natural amino acids into the naturally occurring (wild-type) FGF21 protein sequence or the sequences of the FGF21 variants of the invention. The non-natural amino acid residue also can be incorporated such that a desired functionality is imparted to the FGF21 molecule, for example, the ability to link a functional moiety (e.g., PEG).

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem Soc. 2003 Jan. 29; 125(4):935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

The term "amino acid mimetics," as used herein, refers to chemical compounds that have a structure that is different from the general chemical structure of an amino acid, but functions in a manner similar to a naturally occurring amino acid.

The term "biologically active FGF21 variant" refers to any FGF21 polypeptide variant described herein that possesses an activity of the wild-type FGF21 polypeptide, such as the ability to lower blood glucose, insulin, triglyceride, or cholesterol; reduce body weight; and to improve glucose tolerance, energy expenditure, or insulin sensitivity, regardless of the type or number of modifications that have been introduced into the FGF21 polypeptide variant. FGF21 polypeptide variants possessing a somewhat decreased level of FGF21 activity relative to the wild-type FGF21 polypeptide can nonetheless be considered to be biologically active FGF21 polypeptide variants.

The terms "effective amount" and "therapeutically effective amount" each refer to the amount of an FGF21 protein variant used to support an observable level of one or more biological activities of the wild-type FGF21 polypeptide, such as the ability to lower blood glucose, insulin, triglyceride or cholesterol levels; reduce liver triglyceride or lipid levels; reduce body weight; or improve glucose tolerance, energy expenditure, or insulin sensitivity. For example, a "therapeutically-effective amount" administered to a patient exhibiting, suffering, or prone to suffer from metabolic diseases associated with insulin resistance (such as type 1 or type 2 diabetes mellitus, obesity, or metabolic syndrome), is such an amount which induces, ameliorates or otherwise causes an improvement in the pathological symptoms, disease progression, physiological conditions associated with or resistance to succumbing to the afore mentioned disorders. For the purposes of the present invention a "subject" or "patient" is preferably a human, but can also be an animal, more specifically, a companion animal (e.g., dogs, cats, and the like), farm animals (e.g., cows, sheep, pigs, horses, and the like) and laboratory animals (e.g., rats, mice, guinea pigs, and the like).

The term "pharmaceutically acceptable carrier" or "physiologically acceptable carrier" as used herein refers to one or more formulation materials suitable for accomplishing or enhancing the delivery of an FGF21 protein, fusion, or variant.

The term "antigen" refers to a molecule or a portion of a molecule that is capable of being bound by an antibody, and additionally that is capable of being used in an animal to produce antibodies that are capable of binding to an epitope of that antigen. An antigen may have one or more epitopes.

The term "native Fc" refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG (see Ellison et al., 1982, Nucleic Acids Res. 10: 4071-9). The term "native Fc" as used herein is generic to the monomeric, dimeric, and multimeric forms. The term "Fc variant" refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the fusion molecules of the FGF21 mutants of the present invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be fused to FGF21 or a FGF21 mutant (including a truncated form of FGF21 or a FGF21 mutant) via, for example, a covalent bond between the Fc domain and the FGF21 sequence. Such fusion proteins can form multimers via the association of the Fc domains and both these fusion proteins and their multimers are an aspect of the present invention.

The term "polyethylene glycol" or "PEG" refers to a polyalkylene glycol compound or a derivative thereof, with or without coupling agents or derivatization with coupling or activating moieties.

The term "metabolic diseases associated with insulin resistance," and terms similarly used herein, includes but is not limited to type 1 diabetes mellitus, insulin receptor mutation disorders (INSR disorders), mixed dyslipidemia, nonalcoholic fatty liver disease (NAFLD), insulin resistance, and lipodystrophy.

The terms "insulin receptor disorders (INSR disorders)," "disorders associated with severe inactivating mutations in the insulin receptor," "metabolic diseases associated with insulin resistance," and terms similarly used herein, describe conditions in subjects afflicted with mutations in the insulin receptor (or possibly, proteins directly downstream from it, e.g., IRS1 & IRS2) which cause severe insulin resistance but are often seen without the obesity common in Type 2 diabetes mellitus. Subjects thereby afflicted fall into several categories of roughly increasing severity, including: Type A Insulin Resistance, Type C Insulin Resistance (also known as HAIR-AN Syndrome), Rabson-Mendenhall Syndrome, and finally, Donohue's Syndrome, or Leprechaunism. Type B Insulin Resistance is also included in the general term "Insulin Receptor Disorder" and has a similar phenotype to the genetic forms of insulin resistance outlined herein, except that it is instead caused by neutralizing auto-antibodies to the insulin receptor, as opposed to inactivating mutations.

These disorders are associated with very high endogenous insulin levels, and very often, hyperglycemia. Subjects thereby afflicted also present with various clinical features associated with "insulin toxicity," including hyperandrogenism, polycystic ovary syndrome (PCOS, which is characterized by an increased incidence of insulin receptor mutations), hirsutism, and acanthosis nigricans (excessive growth and pigmentation) in the folds of the skin.

"Type 2 diabetes mellitus" is a condition characterized by excess glucose production in spite of the availability of insulin, and circulating glucose levels remain excessively high as a result of inadequate glucose clearance (insulin action).

"Type 1 diabetes mellitus" is a condition characterized by high blood glucose levels caused by total lack of insulin. This occurs when the body's immune system attacks the insulin-producing beta cells in the pancreas and destroys them. The pancreas then produces little or no insulin. Pancreatic removal or disease may also lead to loss of insulin-producing beta cells.

"Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

"Glucose intolerance," or Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

"HAART" Highly Active Anti-Retroviral Therapy used to treat patients with HIV infection.

"HIV-HAART Induced Partial Lipodystrophy" Adverse effects, including metabolic dysregulation and changes in body fat deposition characterized by insulin resistance, dyslipidemia, lipodystrophy, and increased visceral adiposity, which contribute to an increased risk of cardiovascular disease among HIV patients treated with HAART.

"Hyperglycemia" is defined as an excess of sugar (glucose) in the blood.

"Hypoglycemia", also called low blood sugar, occurs when blood glucose levels drop too low to provide enough energy to maintain normal body function.

"Hyperinsulinemia" is defined as a higher-than-normal level of insulin in the blood.

"Insulin resistance" is defined as a state in which a normal amount of insulin produces a subnormal biologic response.

"Obesity," in terms of the human adult subject, can be defined as a Body Mass Index (BMI) exceeding 30 kg/m2.

"Metabolic syndrome" can be defined as a cluster of at least three of the following signs: abdominal fat—men, a greater than 40-inch waist and women, greater than 35-inch waist; high blood sugar—at least 100 milligrams per deciliter (mg/dL) after fasting; high triglycerides—at least 150 mg/dL in the bloodstream; low HDL—less than 40 mg/dL for males and less than 50 mg/dL for females; and, blood pressure of 130/85 mmHg or higher.

"Hypertension" or high blood pressure that is a transitory or sustained elevation of systemic arterial blood pressure to a level likely to induce cardiovascular damage or other adverse consequences. Hypertension has been arbitrarily defined as a systolic blood pressure above 140 mmHg or a diastolic blood pressure above 90 mmHg.

"Cardiovascular diseases" are diseases related to the heart or blood vessels.

"Atherosclerosis" is a vascular disease characterized by irregularly distributed lipid deposits called plaque in the intima of large and medium-sized arteries that may cause narrowing of arterial lumens and proceed to fibrosis and calcification. Lesions are usually focal and progress slowly and intermittently. Occasionally plaque rupture occurs leading to obstruction of blood flow resulting in tissue death distal to the obstruction. Limitation of blood flow accounts for most clinical manifestations, which vary with the distribution and severity of the obstruction.

"Stroke" is any acute clinical event, related to impairment of cerebral circulation, that lasts longer than 24 hours. A stroke involves irreversible brain damage, the type and severity of symptoms depending on the location and extent of brain tissue whose circulation has been compromised.

"Heart failure", also called congestive heart failure, is a condition in which the heart can no longer pump enough blood to the rest of the body to meet demand.

"Coronary heart disease", also called coronary artery disease, refers to atherosclerotic lesions or plaque in coronary arteries which may cause narrowing of the small blood vessels that supply blood and oxygen to the heart.

"Kidney disease" or nephropathy is any disease of the kidney. Diabetic nephropathy is a major cause of morbidity and mortality in people with type 1 or type 2 diabetes mellitus.

"Diabetic complications" are problems, caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfunction and problems with teeth and gums.

"Neuropathies" are any diseases involving the cranial nerves or the peripheral or autonomic nervous system.

"Gastroparesis" is weakness of gastric peristalsis, which results in delayed gastric emptying.

As used herein, the singular forms "a," "an" and "the" include plural references unless the content clearly dictates otherwise. Thus, for example, reference to "an antibody" includes a mixture of two or more such antibodies.

As used herein, the term "about" refers to +/−20%, +/−10%, or +/−5% of a value.

The terms "polypeptide" and "protein", are used interchangeably and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "individual," "subject," "host," and "patient" are used interchangeably and refer to any subject for whom diagnosis, treatment, or therapy is desired, particularly humans. Other subjects may include cattle, dogs, cats, guinea pigs, rabbits, rats, mice, horses, and the like. In some preferred embodiments the subject is a human.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, and saccharides.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, the ability to lower blood glucose, insulin, triglyceride, or cholesterol levels; to reduce liver lipid or liver triglyceride levels; to reduce body weight; and to improve glucose tolerance, energy expenditure, or insulin sensitivity.

As used herein, the term "modulator" refers to a composition that modulates one or more physiological or biochemical events associated with a metabolic diseases associated with insulin resistance, such as type 1 diabetes mellitus or a metabolic condition like obesity. Said events include but are not limited to the ability to lower blood glucose, insulin, triglyceride, or cholesterol levels; to reduce liver lipid or liver triglyceride levels; to reduce body weight; and to improve glucose tolerance, energy expenditure, or insulin sensitivity.

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e. cDNA of the RNA). A gene product may be made enzymatically, recombinantly, chemically, or within a cell to which the gene is native. In some embodiments, if the gene product is proteinaceous, it exhibits a biological activity. In some embodiments, if the gene product is a nucleic acid, it can be translated into a proteinaceous gene product that exhibits a biological activity.

"Modulation of FGF21 activity," as used herein, refers to an increase or decrease in FGF21 activity that can be a result of, for example, interaction of an agent with an FGF21 polynucleotide or polypeptide, inhibition of FGF21 transcription and/or translation (e.g., through antisense or siRNA interaction with the FGF21 gene or FGF21 transcript, through modulation of transcription factors that facilitate FGF21 expression), and the like. For example, modulation of a biological activity refers to an increase or a decrease in a biological activity. FGF21 activity can be assessed by means including, without limitation, assaying blood glucose, insulin, triglyceride, or cholesterol levels in a subject, assessing FGF21 polypeptide levels, or by assessing FGF21 transcription levels. Comparisons of FGF21 activity can also be accomplished by, e.g., measuring levels of an FGF21 downstream biomarker, and measuring increases in FGF21 signaling. FGF21 activity can also be assessed by measuring: cell signaling; kinase activity; glucose uptake into adipocytes; blood insulin, triglyceride, or cholesterol level fluctuations; liver lipid or liver triglyceride level changes; interactions between FGF21 and an FGF21 receptor; or phosphorylation of an FGF21 receptor. In some embodiments phosphorylation of an FGF21 receptor can be tyrosine phosphorylation. In some embodiments modulation of FGF21 activity can cause modulation of an FGF21-related phenotype.

A "FGF21 downstream biomarker," as used herein, is a gene or gene product, or measurable indicia of a gene or gene product. In some embodiments, a gene or activity that is a downstream marker of FGF21 exhibits an altered level of expression, or in a vascular tissue. In some embodiments, an activity of the downstream marker is altered in the presence of an FGF21 modulator. In some embodiments, the downstream markers exhibit altered levels of expression when FGF21 is perturbed with an FGF21 modulator of the present invention. FGF21 downstream markers include, without limitation, glucose or 2-deoxy-glucose uptake, pERK and other phosphorylated or acetylated proteins or NAD levels.

As used herein, the term "up-regulates" refers to an increase, activation or stimulation of an activity or quantity. For example, in the context of the present invention, FGF21 modulators may increase the activity of an FGF21 receptor. In one embodiment, one or more of FGFR-1c, FGFR-2c, FGFR-3c, or B-klotho may be upregulated in response to an FGF21 modulator. Upregulation can also refer to an FGF21-related activity, such as e.g., the ability to lower blood glucose, insulin, triglyceride, or cholesterol levels; to reduce liver lipid or triglyceride levels; to reduce body weight; to improve glucose tolerance, energy expenditure, or insulin sensitivity; or to cause phosphorylation of an FGF21 receptor; or to increase an FGF21 downstream marker. The FGFR21 receptor can be one or more of FGFR-1c, FGFR-2c, FGFR-3c, or B-klotho. Up-regulation may be at least 25%, at least 50%, at least 75%, at least 100%, at least 150%, at least 200%, at least 250%, at least 400%, or at least 500% as compared to a control.

As used herein, the term "N-terminus" refers to at least the first 10 amino acids of a protein.

As used herein, the terms "N-terminal domain" and "N-terminal region" are used interchangeably and refer to a fragment of a protein that begins at the first amino acid of the protein and ends at any amino acid in the N-terminal half of the protein. For example, the N-terminal domain of FGF21 is from amino acid 1 of wild type FGF21 to any amino acid between about amino acids 10 and 15 of wild type FGF21.

As used herein, the term "C-terminus" refers to at least the last 10 amino acids of a protein.

As used herein, the terms "C-terminal domain" and "C-terminal region" are used interchangeably and refer to a fragment of a protein that begins at any amino acid in the C-terminal half of the protein and ends at the last amino acid of the protein. For example, the C-terminal domain of FGF21 begins at any amino acid from amino acid 105 to about amino acid 200 of wild type FGF21 and ends at amino acid 209 of wild type FGF21.

The term "domain" as used herein refers to a structural part of a biomolecule that contributes to a known or suspected function of the biomolecule. Domains may be co-extensive with regions or portions thereof and may also incorporate a portion of a biomolecule that is distinct from a particular region, in addition to all or part of that region.

As used herein, the term "signal domain" (also called "signal sequence" or "signal peptide") refers to a peptide domain that resides in a continuous stretch of amino acid sequence at the N-terminal region of a precursor protein (often a membrane-bound or secreted protein) and is involved in post-translational protein transport. In many cases the signal domain is removed from the full-length protein by specialized signal peptidases after the sorting process has been completed. Each signal domain specifies a particular destination in the cell for the precursor protein. The signal domain of FGF21 is amino acids 1-28.

As used herein, the term "receptor binding domain" refers to any portion or region of a protein that contacts a membrane-bound receptor protein, resulting in a cellular response, such as a signaling event.

As used herein, the term "ligand binding domain" refers to any portion or region of a protein retaining at least one qualitative binding activity of a corresponding native sequence of FGF21.

The term "region" refers to a physically contiguous portion of the primary structure of a biomolecule. In the case of proteins, a region is defined by a contiguous portion of the amino acid sequence of that protein. In some embodiments a "region" is associated with a function of the biomolecule.

The term "fragment" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity.

A "native sequence" polypeptide is one that has the same amino acid sequence as a polypeptide derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Naturally occurring disulfide bonds, as provided by cysteine residues, generally increase thermodynamic stability of proteins. Successful examples of increased thermodynamic stability, as measured in increase of the melting temperature, are multiple disulfide-bonded mutants of the enzymes T4 lysozyme (Matsumura, et al., PNAS 86:6562-6566 (1989)) and barnase (Johnson et al., J. Mol. Biol. 268: 198-208 (1997)). An aspect of the present invention is an enhancement of the physical stability of FGF21 in the presence of a preservative, achieved by the presence of disulfide bonds within the variants, which constrain the flexibility of wild type FGF21 and thereby limit access of the preservative to the hydrophobic core of the protein.

The present invention provides methods of treatment that comprise variants or mutants of wild type human FGF21, or a biologically active peptide thereof, with enhanced pharmaceutical stability engendered by the incorporation of additional disulfide bonds, e.g., via incorporating or substituting cysteine residues into the wild-type FGF21 protein or the polypeptide and protein variants of the invention. One skilled in the art will recognize that the native cysteines, cysteine 103 and cysteine 121, could be utilized as loci to introduce a novel disulfide bond that may impart improved properties, in addition to the suggested embodiments described herein and in the literature.

The methods of the present invention comprise pharmaceutical compositions that may be administered by any means that achieve the generally intended purpose: to treat metabolic diseases associated with insulin resistance, such as type 2 diabetes mellitus, insulin receptor mutation disorders (INSR disorders), nonalcoholic fatty liver disease (NAFLD) and various forms of partial lipodystrophy including familial partial lipodystrophy and HIV HAART induced partial lipodystrophy as well as diseases associated with insulin production (i.e., type 1 diabetes mellitus). The term "parenteral" as used herein refers to modes of administration that include intravenous, intramuscular, intraperitoneal, intrasternal, subcutaneous, and intraarticular injection and infusion. The dosage administered will be dependent upon the age, health, and weight of the recipient, kind of concurrent treatment, if any, frequency of treatment, and the nature of the effect desired. Included are all compositions wherein an FGF21 polypeptide or protein, or fusion, mutant, or variant thereof, is present in an amount that is effective to achieve the desired medical effect for treatment of metabolic diseases associated with insulin resistance. While individual needs may vary from one patient to another, the determination of the optimal ranges of effective amounts of all of the components is within the ability of the clinician of ordinary skill.

The variants of FGF21 comprising the methods of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [Remington's Pharmaceutical Sciences 16th edition (1980)]. The variants of the present invention may be combined with a pharmaceutically acceptable buffer, and the pH adjusted to provide acceptable stability, and a pH acceptable for administration.

For parenteral administration, in one embodiment, FGF21 variants are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising an FGF21 variant, as determined by good medical practice and the clinical condition of the individual patient. A typical dose range for the FGF21 variants of the present invention will range from about 0.01 mg per day to about 1000 mg per day (or about 0.07 mg per week to about 7000 mg per week administered once per week) for an adult. Preferably, the dosage ranges from about 0.1 mg per day to about 100 mg per day (or about 0.7 mg per week to about 700 mg per week administered once per week), more preferably from about 1.0 mg/day to about 10 mg/day (or about 7 mg per week to about 70 mg per week administered once per week). Most preferably, the dosage is about 1-5 mg/day (or about 7 mg per week to about 35 mg per week administered once per week). The appropriate dose of an FGF21 variant administered according to the claimed methods of the invention will improve metabolic profiles, e.g., will lower blood glucose levels, increase energy expenditure, and/or promote more efficient glucose utilization, and thus is useful for treating metabolic diseases associated with insulin resistance, such as type 2 diabetes mellitus, insulin receptor mutation disorders (INSR disorders), nonalcoholic fatty liver disease (NAFLD) and various forms of partial lipodystrophy including familial partial lipodystrophy and HIV-HAART induced partial lipodystrophy as well as diseases associated with insulin production (type 1 diabetes mellitus).

In addition, because hyperglycemia and insulin resistance are common in critically ill patients given nutritional support, some ICUs administer insulin to treat excessive hyperglycemia in fed critically ill patients. In fact, recent studies document the use of exogenous insulin to maintain blood glucose at a level no higher than 110 mg per deciliter reduced morbidity and mortality among critically ill patients in the surgical intensive care unit, regardless of whether they had a history of diabetes (Van den Berghe, et al. N Engl J Med., 345(19): 1359, (2001)). Thus, methods of the present invention are uniquely suited to help restore metabolic stability in metabolically unstable critically ill patients.

In another aspect of the present invention, variants of FGF21 for use as a medicament for the treatment of metabolic diseases associated with insulin resistance, such as type 2 diabetes mellitus, insulin receptor mutation disorders (INSR disorders), nonalcoholic fatty liver disease (NAFLD), and various forms of partial lipodystrophy including familial partial lipodystrophy and HIV-HAART induced partial lipodystrophy as well as diseases associated with insulin production (type 1 diabetes mellitus), and in reducing the mortality and morbidity of critically ill patients.

Having now described the present invention in detail, the same will be more clearly understood by reference to the following examples, which are included herewith for purposes of illustration only and are not intended to be limiting of the invention.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pennsylvania: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

Site-Specific FGF21 Mutants

The term "site-specific FGF21 mutant" or "substituted FGF21 mutant" refers to a FGF21 mutant polypeptide having an amino acid sequence that differs from the amino acid sequence of a naturally occurring FGF21 polypeptide sequence, e.g., having NCBI reference sequence number NP_061986.1, and variants thereof. Site-specific FGF21 mutants can be generated by introducing amino acid substitutions, either conservative or non-conservative and using naturally or non-naturally occurring amino acids, at particular positions of the FGF21 polypeptide.

"Conservative amino acid substitution" can involve a substitution of a native amino acid residue (i.e., a residue found in a given position of the wild-type FGF21 polypeptide sequence) with a nonnative residue (i.e., a residue that is not found in a given position of the wild-type FGF21 polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:

(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro;
(6) aromatic: Trp, Tyr, Phe; and
(7) selenocysteine, pyrrolysine (PYL), and pyrroline-carboxy-lysine (PCL).

Conservative substitutions can involve the exchange of a member of one of these classes for another member of the same class. Non-conservative substitutions can involve the exchange of a member of one of these classes for a member from another class.

Desired amino acid substitutions (whether conservative or non-conservative) can be determined by those skilled in the art at the time such substitutions are desired.

Truncated FGF21 Polypeptides

One embodiment of the present invention is directed to methods of treatment comprising truncated forms of the mature FGF21 polypeptide. This embodiment of the present invention arose from an effort to identify truncated FGF21 polypeptides that are capable of providing an activity that is similar, and in some instances superior, to untruncated forms of the mature FGF21 polypeptide.

As used herein, the term "truncated FGF21 polypeptide" refers to an FGF21 polypeptide in which amino acid residues have been removed from the amino-terminal (or N-terminal) end of the FGF21 polypeptide, amino acid residues have been removed from the carboxyl-terminal (or C-terminal) end of the FGF21 polypeptide, or amino acid residues have been removed from both the amino-terminal and carboxyl-terminal ends of the FGF21 polypeptide. The various truncations disclosed herein were prepared as described herein.

The activity of N-terminally truncated FGF21 polypeptides and C-terminally truncated FGF21 polypeptides can be assayed using an in vitro phospho-ERK assay. Specific details of the in vitro assays that can be used to examine the activity of truncated FGF21 polypeptides can be found in the examples.

The activity of the truncated FGF21 polypeptides of the present invention can also be assessed in an in vivo assay, such as ob/ob mice. Generally, to assess the in vivo activity of a truncated FGF21 polypeptide, the truncated FGF21 polypeptide can be administered to a test animal intraperitoneally. After a desired incubation period (e.g., one hour or more), a blood sample can be drawn, and blood glucose levels can be measured.

a. N-Terminal Truncations

Some embodiments of the methods of the present invention comprise N-terminal truncations with 1, 2, 3, 4, 5, 6, 7, or 8 amino acid residues from the N-terminal end of the mature FGF21 polypeptide. Truncated FGF21 polypeptides having N-terminal truncations of fewer than 9 amino acid residues retain the ability of the mature FGF21 polypeptide to lower blood glucose in an individual. Accordingly, in particular embodiments, the present invention encompasses truncated forms of the mature FGF21 polypeptide or FGF21 protein variants having N-terminal truncations of 1, 2, 3, 4, 5, 6, 7, or 8 amino acid residues.

b. C-Terminal Truncations

Some embodiments of the methods of the present invention comprise C-terminal truncations with 1, 2, 3, 4, 5, 6, 7, 8, 9, 10, 11, or 12 amino acid residues from the C-terminal end of the mature FGF21 polypeptide. Truncated FGF21 polypeptides having C-terminal truncations of fewer than 13 amino acid residues exhibited an efficacy of at least 50% of the efficacy of wild-type FGF21 in an in vitro ELK-luciferase assay (Yie J. et al. FEBS Letts 583: 19-24 (2009)), indicating that these FGF21 mutants retain the ability of the mature FGF21 polypeptide to lower blood glucose in an individual. Accordingly, in particular embodiments, the present invention encompasses truncated forms of the mature FGF21 polypeptide or FGF21 protein variants having C-terminal truncations of 1, 2, 3, 4, 5, 6, 7, 8, 9, 10, 11, or 12 amino acid residues.

c. N-Terminal and C-Terminal Truncations

Some embodiments of the methods of the present invention comprise truncated FGF21 polypeptides with a combination of N-terminal and C-terminal truncations. Truncated FGF21 polypeptides having a combination of N-terminal and C-terminal truncations share the activity of corresponding truncated FGF21 polypeptides having either the N-terminal or C-terminal truncations alone. In other words, truncated FGF21 polypeptides having both N-terminal truncations of fewer than 9 amino acid residues and C-terminal truncations of fewer than 13 amino acid residues possess similar or greater blood glucose-lowering activity as truncated FGF21 polypeptides having N-terminal truncations of fewer than 9 amino acid residues or truncated FGF21 polypeptides having C-terminal truncations of fewer than 13 amino acid residues. Accordingly, in particular embodiments, the present invention encompasses truncated forms of the mature FGF21 polypeptide or FGF21 protein variants having both N-terminal truncations of 1, 2, 3, 4, 5, 6, 7, or 8 amino acid residues and C-terminal truncations of 1, 2, 3, 4, 5, 6, 7, 8, 9, 10, 11, or 12 amino acid residues.

As with all FGF21 variants of the methods of the present invention, truncated FGF21 polypeptides can optionally comprise an amino-terminal methionine residue, which can be introduced by directed mutation or as a result of a bacterial expression process.

The truncated FGF21 polypeptides comprising the methods of the present invention can be prepared as described in the examples described herein. Those of ordinary skill in the art, familiar with standard molecular biology techniques, can employ that knowledge, coupled with the instant disclosure, to make and use the truncated FGF21 polypeptides of the present invention. Standard techniques can be used for recombinant DNA, oligonucleotide synthesis, tissue culture, and transformation (e.g., electroporation, lipofection). See, e.g., Sambrook et al., Molecular Cloning: A Laboratory Manual, supra, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses; chemical analyses; pharmaceutical preparation, formulation, and delivery; and treatment of patients.

The truncated FGF21 polypeptides of the methods of the present invention can also be fused to another entity, which can impart additional properties to the truncated FGF21 polypeptide. In one embodiment of the present invention, a truncated FGF21 polypeptide can be fused to an IgG constant domain or fragment thereof (e.g., the Fc region), Human Serum Albumin (HSA), or albumin-binding polypeptides. Such fusion can be accomplished using known molecular biological methods and/or the guidance provided herein. The benefits of such fusion polypeptides, as well as methods for making such fusion polypeptides, are discussed in more detail herein.

FGF21 Fusion Proteins

As used herein, the term "FGF21 fusion polypeptide" or "FGF21 fusion protein" refers to a fusion of one or more amino acid residues (such as a heterologous protein or peptide) at the N-terminus or C-terminus of any FGF21 protein variant described herein.

Heterologous peptides and polypeptides include, but are not limited to, an epitope to allow for the detection and/or isolation of an FGF21 protein variant; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; a functional or non-functional antibody, or a heavy or light chain thereof; and a polypeptide which has an activity, such as a therapeutic activity, different from the FGF21 protein variants of the present invention. Also encompassed by the present invention are FGF21 mutants fused to human serum albumin (HSA).

FGF21 fusion proteins can be made by fusing heterologous sequences at either the N-terminus or at the C-terminus of an FGF21 protein variant. As described herein, a heterologous sequence can be an amino acid sequence or a non-amino acid-containing polymer. Heterologous sequences can be fused either directly to the FGF21 protein variant or via a linker or adapter molecule. A linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). A linker or adapter molecule can also be designed with a cleavage site for a DNA restriction endonuclease or for a protease to allow for the separation of the fused moieties.

a. Fc Fusions

In one embodiment of the present invention, an FGF21 protein variant is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337: 525-31). When joined together with a therapeutic protein, an Fc domain can provide longer half-life or incorporate such functions as Fc receptor binding, protein A binding, complement fixation, and perhaps even placental transfer (Capon et al., 1989).

In vivo pharmacokinetic analysis indicated that human FGF21 has a short half-life of about 0.5 to 1 hours in mice due to rapid clearance and in vivo degradation. Therefore, to extend the half-life of FGF21 an Fc sequence was fused to the N- or C-terminal end of the FGF21 polypeptide. The fusion of an Fc region to wild-type FGF21, in particularly Fc fused to the N-terminus of wild-type FGF21, did not extend the half-life as expected, however, which led to an investigation of the proteolytic degradation of FGF21 in vivo and the identification of FGF21 mutants that were resistant to such degradation.

Throughout the disclosure, Fc-FGF21 refers to a fusion protein in which the Fc sequence is fused to the N-terminus of FGF21. Similarly, throughout the disclosure, FGF21-Fc refers to a fusion protein in which the Fc sequence is fused to the C-terminus of FGF21.

The resulting FGF21 fusion protein can be purified, for example, by the use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in International Publication No. WO 00/024782, which is hereby incorporated by reference in its entirety. This document discusses linkage to a "vehicle" such as polyethylene glycol (PEG), dextran, or an Fc region.

b. Fusion Protein Linkers

When forming the fusion proteins of the present invention, a linker can, but need not, be employed. When present, the linker's chemical structure may not critical, since it serves primarily as a spacer. The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, and lysine. In some embodiments, a linker is made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)). While a linker of 15 amino acid residues has been found to work particularly well for FGF21 fusion proteins, the present invention contemplates linkers of any length or composition.

The linkers described herein are exemplary, and linkers that are much longer and which include other residues are contemplated by the present invention. Non-peptide linkers are also contemplated by the present invention. For example, alkyl linkers such as can be used. These alkyl linkers can further be substituted by any non-sterically hindering group, including, but not limited to, a lower alkyl (e.g., C1-C6), lower acyl, halogen (e.g., Cl, Br), CN, NH2, or phenyl. An exemplary non-peptide linker is a polyethylene glycol linker, wherein the linker has a molecular weight of 100 to 5000 kD, for example, 100 to 500 kD.

Chemically-Modified FGF21 Mutants

Chemically modified forms of the FGF21 protein variants described herein, including the truncated forms of FGF21 described herein, can be prepared by one skilled in the art, given the disclosures described herein. Such chemically modified FGF21 mutants are altered such that the chemically modified FGF21 mutant is different from the unmodified FGF21 mutant, either in the type or location of the molecules naturally attached to the FGF21 mutant. Chemically modified FGF21 mutants can include molecules formed by the deletion of one or more naturally-attached chemical groups.

In one embodiment, FGF21 protein variants of the present invention can be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable. Non-water soluble polymers conjugated to FGF21 protein variants of the present invention also form an aspect of the invention.

Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 12 kDa and about 40 kDa, and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-(C1-C10), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached FGF21 protein variant multimers. Also encompassed by the present invention are FGF21 mutants covalently attached to polysialic acid.

In some embodiments of the present invention, an FGF21 mutant is covalently, or chemically, modified to include one or more water-soluble polymers, including, but not limited to, polyethylene glycol (PEG), polyoxyethylene glycol, or polypropylene glycol. See, e.g., U.S. Pat. Nos. 4,640,835; 4,496,689; 4,301,144; 4,670,417; 4,791,192; and 4,179,337. In some embodiments of the present invention, an FGF21 mutant comprises one or more polymers, including, but not limited to, monomethoxy-polyethylene glycol, dextran, cellulose, another carbohydrate-based polymer, poly-(N-vinyl pyrrolidone)-polyethylene glycol, propylene glycol homopolymers, a polypropylene oxide/ethylene oxide co-polymer, polyoxyethylated polyols (e.g., glycerol), polyvinyl alcohol, or mixtures of such polymers.

In some embodiments of the present invention, an FGF21 mutant is covalently-modified with PEG subunits. In some embodiments, one or more water-soluble polymers are bonded at one or more specific positions (for example, at the N-terminus) of the FGF21 mutant. In some embodiments, one or more water-soluble polymers are randomly attached to one or more side chains of an FGF21 mutant. In some embodiments, PEG is used to improve the therapeutic capacity of an FGF21 mutant. Certain such methods are discussed, for example, in U.S. Pat. No. 6,133,426, which is hereby incorporated by reference for any purpose.

In embodiments of the present invention wherein the polymer is PEG, the PEG group can be of any convenient molecular weight, and can be linear or branched. The average molecular weight of the PEG group will preferably range from about 2 kD to about 100 kDa, and more preferably from about 5 kDa to about 50 kDa, e.g., 10, 20, 30, 40, or 50 kDa. The PEG groups will generally be attached to the FGF21 mutant via acylation or reductive alkylation through a reactive group on the PEG moiety (e.g., an aldehyde, amino, thiol, or ester group) to a reactive group on the FGF21 mutant (e.g., an aldehyde, amino, or ester group).

Branched PEG derivatives, also known as "Y-shaped" PEG derivatives, contain two linear methoxy PEG chain attached to a central core. The sterically bulky structure of these "Y-shaped" PEG derivatives will facilitate the single point attachment of the modified molecules. By way of example, three kinds of "Y-shaped" PEG derivatives are Y-NHS-40K (useful for amine PEGylation); Y-MAL-40K (useful for thiol PEGylation); and Y-ALD-40K (e.g., Y-AALD-40K and Y-PALD-40K)(useful for N-terminal PEGylation). For amine PEGylation, the "Y-shape" NHS ester will react with the amino group of lysine(s) or the N-terminal amine in biological active molecules to produce a stable amide linkage(s). This NHS ester will couple with the targeted molecules at pH 7-8. For thiol PEGylation, the "Y-shape" maleimide will react with the thiol groups in biological active molecules to generates a stable 3-thiosuccinimidyl ether linkage. This maleimide will couple with the targeted molecules at pH 5.0-6.5 in the presence of other functional groups. For N-terminal PEGylation, The "Y-shape" aldehyde will preferably react with the N-terminal amine in biological active molecules to produce a stable amine linkage in the presence of a reducing reagent such as sodium cyanoborohydride. This aldehyde will couple with the N-terminal amine of the targeted molecules at pH 5-8. Reagents for performing branched PEGylation are available through, e.g., JenKem Technology.

The PEGylation of a polypeptide, including the FGF21 mutants of the present invention, can be specifically carried out using any of the PEGylation reactions known in the art. Such reactions are described, for example, in the following references: Francis et al., 1992, Focus on Growth Factors 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono C1-C10 alkoxy or aryloxy derivatives thereof (see, e.g., U.S. Pat. No. 5,252,714).

In some embodiments of the present invention, a useful strategy for the attachment of the PEG group to a polypeptide involves combining, through the formation of a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer that can be used for protein modification. Therefore, the FGF21 mutants of the present invention fused to a polysaccharide polymer form embodiments of the present invention. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kD to about 20 kD.

In general, chemical modification can be performed under any suitable condition used to react a protein with an activated polymer molecule. Methods for preparing chemically modified polypeptides will generally comprise the steps of: (a) reacting the polypeptide with the activated polymer molecule (such as a reactive ester or aldehyde derivative of the polymer molecule) under conditions whereby a FGF21 protein variant becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified FGF21 mutants can have a single polymer molecule moiety at the amino-terminus (see, e.g., U.S. Pat. No. 5,234,784)

In another embodiment of the present invention, FGF21 protein variants can be chemically coupled to biotin. The biotin/FGF21 protein variants are then allowed to bind to avidin, resulting in tetravalent avidin/biotin/FGF21 protein variants. FGF21 protein variants can also be covalently coupled to dinitrophenol (DNP) or trinitrophenol (TNP) and the resulting conjugates precipitated with anti-DNP or anti-TNP-IgM to form decametric conjugates with a valency of 10.

Generally, conditions that can be alleviated or modulated by the administration of the present chemically modified FGF21 mutants include those described herein for FGF21 protein variants. However, the chemically modified FGF21 mutants disclosed herein can have additional activities, enhanced or reduced biological activity, or other characteristics, such as increased or decreased half-life, as compared to unmodified FGF21 mutants.

Therapeutic Compositions of FGF21 Mutants and Administration Thereof

Therapeutic compositions comprising FGF21 mutants are within the scope of the methods of the present invention, and are specifically contemplated in light of the identification of several mutant FGF21 sequences exhibiting enhanced properties. Such FGF21 mutant pharmaceutical compositions can comprise a therapeutically effective amount of an FGF21 protein variant in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HC1, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides; preferably sodium or potassium chloride; or mannitol sorbitol), delivery vehicles, diluents, excipients and/or pharmaceutical adjuvants (see, e.g., Remington's Pharmaceutical Sciences (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., Remington's Pharmaceutical Sciences, supra). Such compositions can influence the physical state, stability, rate of in vivo release, and rate of in vivo clearance of the FGF21 protein variant.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, FGF21 protein variant compositions can be prepared for storage by mixing the selected composition having the desired degree of purity with optional formulation agents (Remington's Pharmaceutical Sciences, supra) in the form of a lyophilized cake or an aqueous solution. Further, the FGF21 protein variant product can be formulated as a lyophilizate using appropriate excipients such as sucrose.

The FGF21 protein variant pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired FGF21 protein variant in a pharmaceutically acceptable vehicle. A particularly suitable vehicle for parenteral injection is sterile distilled water in which an FGF21 protein variant is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, an FGF21 protein variant can be formulated as a dry powder for inhalation. FGF21 protein variant inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, FGF21 protein variants that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the FGF21 protein variant. Diluents, flavorings, low melting point waxes, vegetable oils, lubricants, suspending agents, tablet disintegrating agents, and binders can also be employed.

Another pharmaceutical composition can involve an effective quantity of FGF21 protein variants in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional FGF21 protein variant pharmaceutical compositions will be evident to those skilled in the art, including formulations involving FGF21 protein variants in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, Int. J Pharm. 364: 298-327, and Freiberg & Zhu, 2004, Int. J Pharm. 282: 1-18, which discuss microsphere/microparticle preparation and use).

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, Biopolymers 22: 547-56), poly(2-hydroxyethyl-methacrylate) (Langer et al., 1981, J. Biomed. Mater. Res. 15: 167-277 and Langer, 1982, Chem. Tech. 12: 98-105), ethylene vinyl acetate (Langer et al., supra) or poly-D-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

The FGF21 protein variant pharmaceutical composition to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of an FGF21 protein variant pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the FGF21 protein variant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 μg/kg to up to about 100 mg/kg or more, depending on the factors mentioned above. In other embodiments, the dosage can range from 0.1 μg/kg up to about 100 mg/kg; or 1 μg/kg up to about 100 mg/kg; or 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, up to about 100 mg/kg. In yet other embodiments, the dosage can be 50 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 100 μg/kg, 200 μg/kg, 300 μg/kg, 400 μg/kg, 500 μg/kg, 600 μg/kg, 700 μg/kg, 800 μg/kg, 900 μg/kg, 1000 μg/kg, 2000 μg/kg, 3000 μg/kg, 4000 μg/kg, 5000 μg/kg, 6000 μg/kg, 7000 μg/kg, 8000 μg/kg, 9000 μg/kg or 10 mg/kg.

The frequency of dosing will depend upon the pharmacokinetic parameters of the FGF21 protein variant in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Therapeutic Uses of FGF21

FGF21 polypeptide or protein, or mutants, variants, and fusions thereof, can be used to treat, diagnose, ameliorate, or prevent a number of diseases, disorders, or conditions, including, but not limited to treating metabolic diseases associated with insulin resistance, such as type 2 diabetes mellitus, insulin receptor mutation disorders (INSR disorders), nonalcoholic fatty liver disease (NAFLD) and various forms of partial lipodystrophy including familial partial lipodystrophy and HIV-HAART induced partial lipodystrophy as well as diseases associated with insulin production (type 1 diabetes mellitus), and in reducing the mortality and morbidity of critically ill patients.

A disorder or condition such as type 1 diabetes mellitus or insulin receptor mutation disorders can be treated by administering an FGF21 polypeptide or protein, or mutant, variant, or fusion thereof to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the FGF21. It will be apparent to those of skill in the art that a therapeutically effective dose of FGF21 will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of FGF21 mutant polypeptide that elicits the biological or medicinal response in a tissue system, animal, or human being sought by a researcher, medical doctor, or other clinician, which includes alleviation of the symptoms of the disease or disorder being treated.

Pharmaceutical Compositions

The present invention also provides methods comprising pharmaceutical compositions comprising one or more of the FGF21 polypeptide or protein, or mutants, variants, and fusions thereof described herein and a pharmaceutically acceptable carrier. In some embodiments the pharmaceutical compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

Fusion Proteins and FGF21-Derived Peptidic Compounds

In another embodiment, the methods of the present invention comprise FGF21 proteins, variants, or mutants which can be made into a fusion protein or peptidic compound derived from the FGF21 amino acid sequences. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into FGF21 proteins, variants, or mutants, or conjugating FGF21 proteins, variants, or mutants to poly(ethylene glycol)(PEG; pegylation), e.g., via lysine-monopegylation or cysteine-monopegylation. Such techniques have proven to be beneficial in prolonging the half-life of therapeutic protein drugs. It is expected that pegylation of the FGF21 proteins, variants, or mutants comprising the methods of the invention may result in similar pharmaceutical advantages.

In addition, pegylation can be achieved in any part of an FGF21 proteins, variants, or mutants comprising the methods of the invention by the introduction of a nonnatural amino acid. Certain nonnatural amino acids can be introduced by the technology described in Deiters et al., J Am Chem Soc 125:11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the nonnatural amino acid of choice. Particular nonnatural amino acids that are beneficial for purpose of conjugating moieties to the polypeptides of the invention include those with acetylene and azido side chains. The FGF21 proteins, variants, or mutants comprising the methods of the invention containing these novel amino acids can then be pegylated at these chosen sites in the protein.

EXAMPLES

Example 1: In Vivo Administration of FGF21 in Type 1 Diabetes Mouse Models

Human type 1 diabetes (T1D) exhibits high plasma glucose and low insulin levels due to the inability of pancreatic (3-cell to produce and secrete insulin. As a consequence of a very low insulin level in circulation, patients with T1D have reduced utilization of carbohydrate and increased utilization of lipid, which leads to loss of body fat storage and ketosis.

High dosages of the (3-cell toxin streptozocin (STZ) induce severe insulin deficiency and T1D with ketosis and hyperphagia. When high dose STZ is injected to adult animals, (3-cell regeneration is diminished and animals remain in T1D condition.

Diabetes was induced in twenty-two-week old male C57BL mice via an intraperitoneal injection of STZ for 3 consecutive days at 70 mg/kg/day. When being fully diabetic (12-19 days from the first STZ injection), in two separate studies, the mice received either vehicle (PBS) or wild type FGF21 (3 mg/kg/day, subcutaneous injection) for 12 days, or vehicle or Variant 76 two times a week (1 mg or 3 mg/kg, 2×/wk, subcutaneous injection) for 26 days. One group of non-STZ mice was used as normal control for each study. All the animals were acclimated in TSE system for at least 24 h before the RER and energy expenditure measurements.

Groups of mice in Study 1: Normal-vehicle (n=6); STZ-vehicle (n=6); STZ-wild type FGF21(n=6). Groups of mice in Study 2: Normal-vehicle (n=8); STZ-vehicle (n=8); STZ-Cmpd A 1 mg/kg (n=8); STZ-Cmpd A 3 mg/kg (n=8). The following measurements were taken: glucose, insulin, HbA1c, respiratory exchange ratio (RER), energy expenditure, food intake, body weight, epididymal fat mass, and ketone body levels. As seen in Tables 1 and 2 below, STZ treated mice became hyperglycemic and hypoinsulinemic.

Figure 1B:
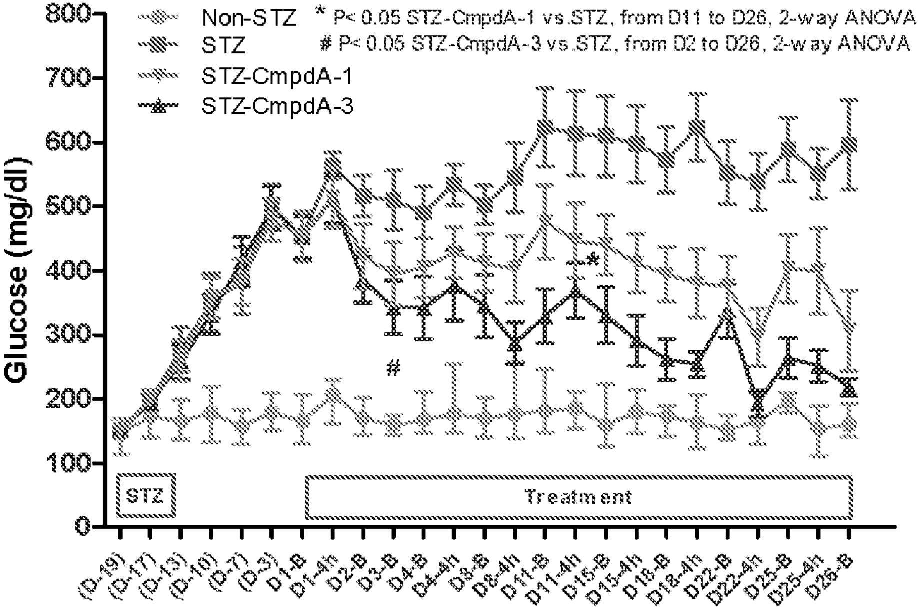
Figure 2:
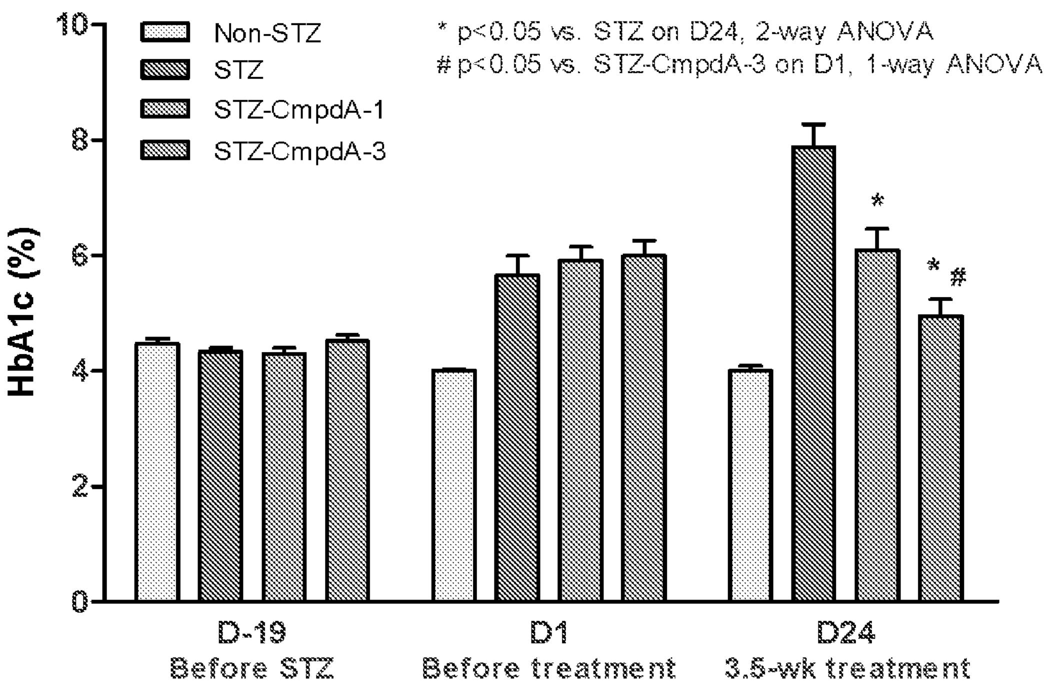
FIG. 2 is a graphical representation showing a change in HbA1c levels. Variant 76 (referred to as Cmpd-A) was administered at both 1 and 3 mg/kg doses, showing reduced HbA1c levels.
Figure 3A:
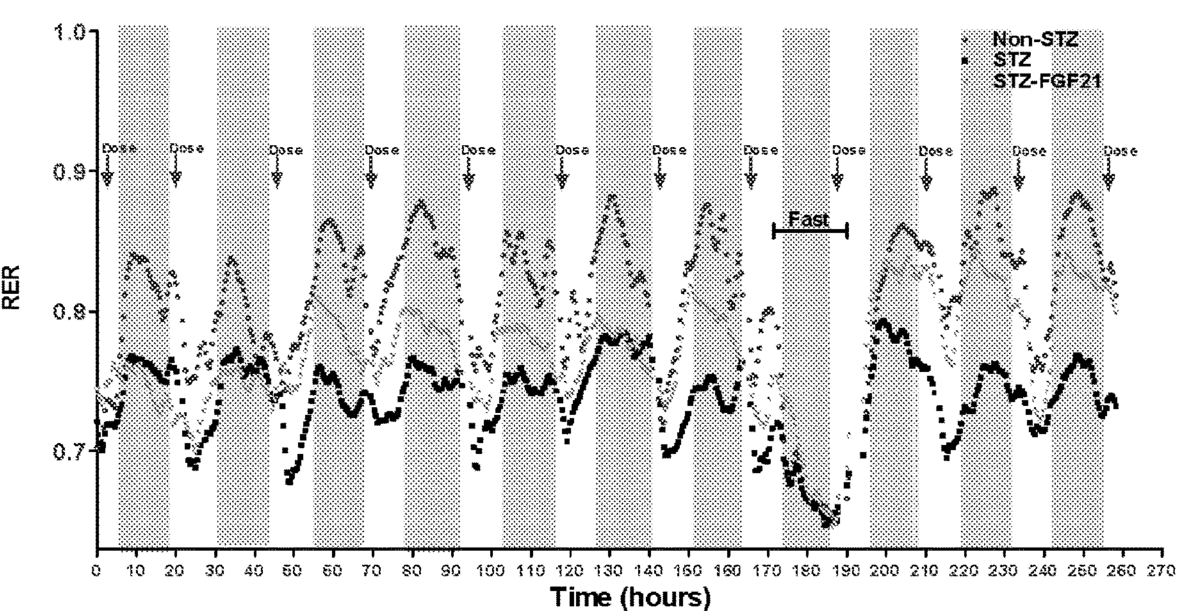
FIGS. 3A and 3B are graphical representations showing a change in respiratory exchange ratio (RER) levels when STZ mice are administered wild type FGF21 (FIG. 3A) and Variant 76 (FIG. 3B). Wild type FGF21 (3 mg/kg, daily dose) increased RER in STZ mice, and Variant 76 (referred to as Cmpd-A)(1 or 3 mg/kg, 2 doses/week) increased glucose utilization in STZ mice.
Figure 3B:
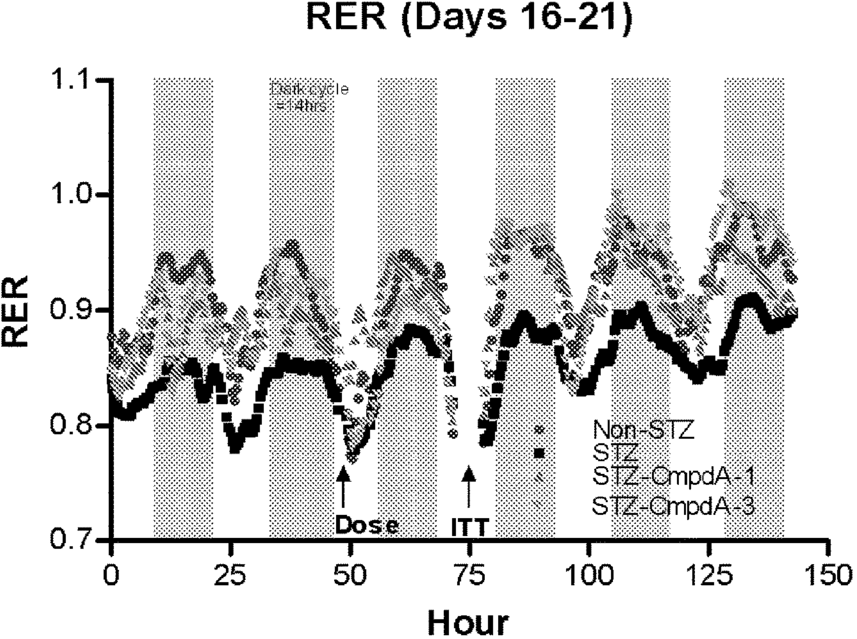
Figure 4A:
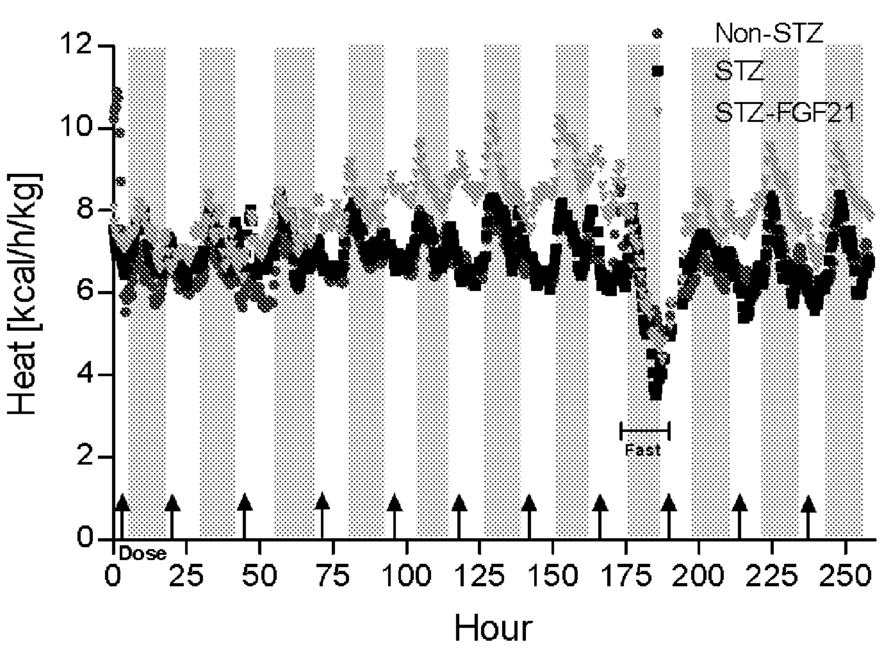
FIGS. 4A and 4B are graphical representations showing a change in energy expenditure levels when STZ mice are administered wild type FGF21 (FIG. 4A) and Variant 76 (FIG. 4B). Wild type FGF21 (3 mg/kg, daily dose) increased energy expenditure in STZ mice, and Variant 76 (referred to as Cmpd-A)(1 or 3 mg/kg, 2 doses/week) increased energy expenditure in STZ mice.
Figure 4B:
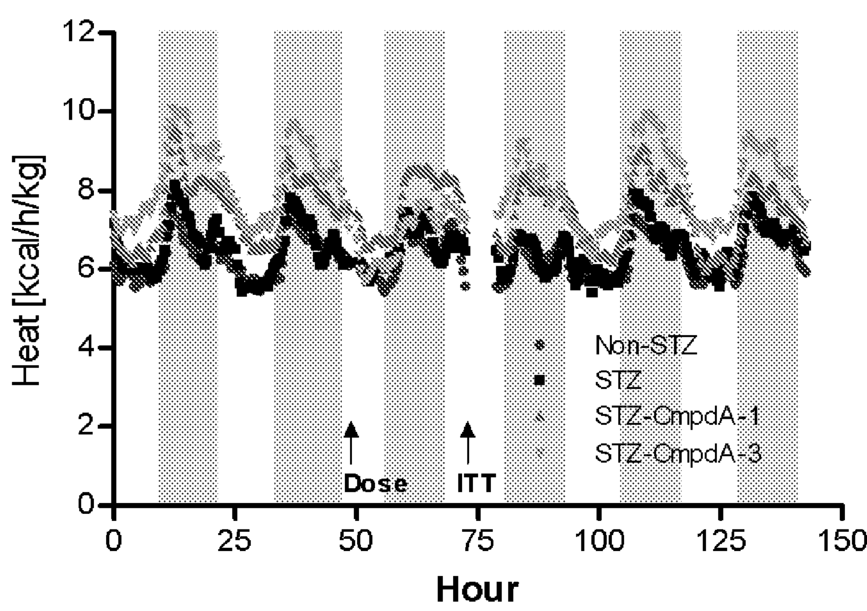
Figure 5A:
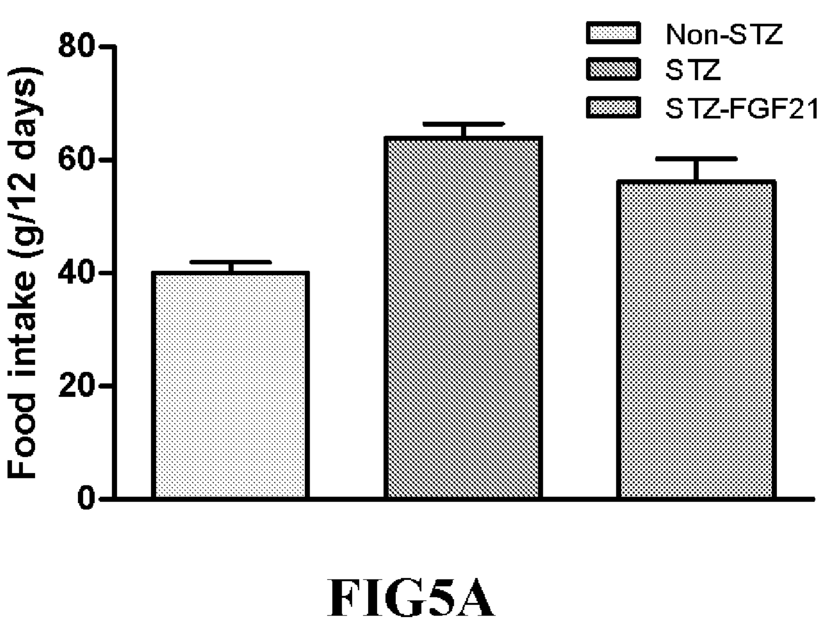
FIGS. 5A and 5B are graphical representations showing a change in food intake when STZ mice are administered wild type FGF21 (FIG. 5A) and Variant 76 (Cmpd-A) (FIG. 5B). Both wild type FGF21 (3 mg/kg, daily dose) and Variant 76 (1 or 3 mg/kg, 2 doses/week) decreased cumulative food intake in STZ mice.
Figure 5B:
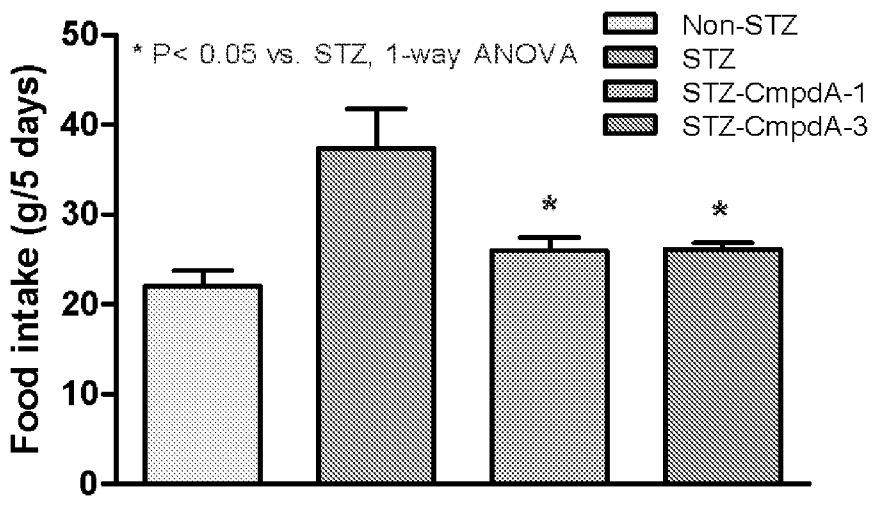
Figure 6A:
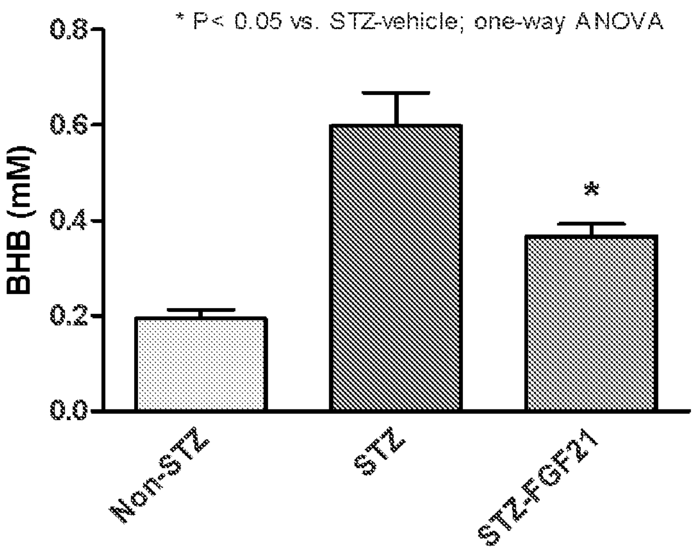
FIGS. 6A and 6B are graphical representations showing a change in ketogenesis when STZ mice are administered wild type FGF21 (FIG. 6A) and Variant 76 (referred to as Cmpd-A)(FIG. 6B). Both wild type FGF21 (3 mg/kg, daily dose) and Variant 76 (1 or 3 mg/kg, 2 doses/week) decreased ketogenesis in STZ mice.
Figure 6B:
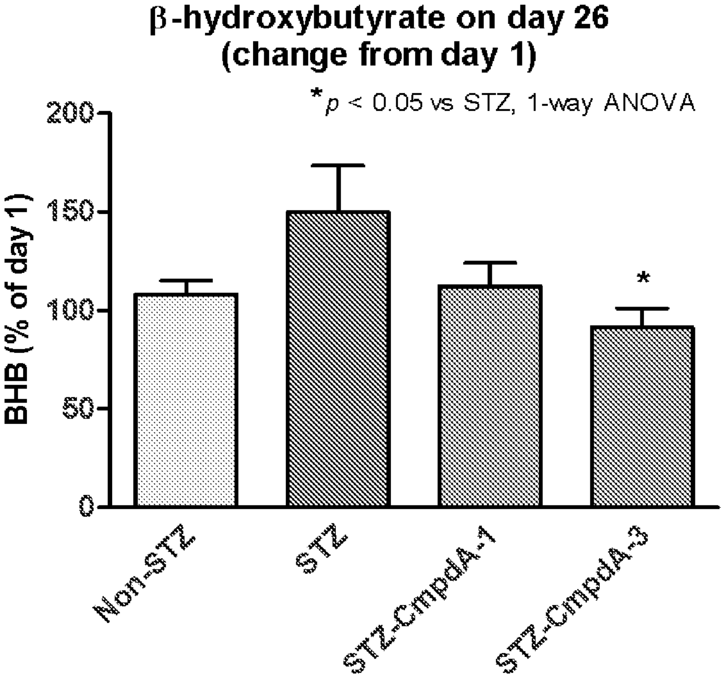
Figure 7A:
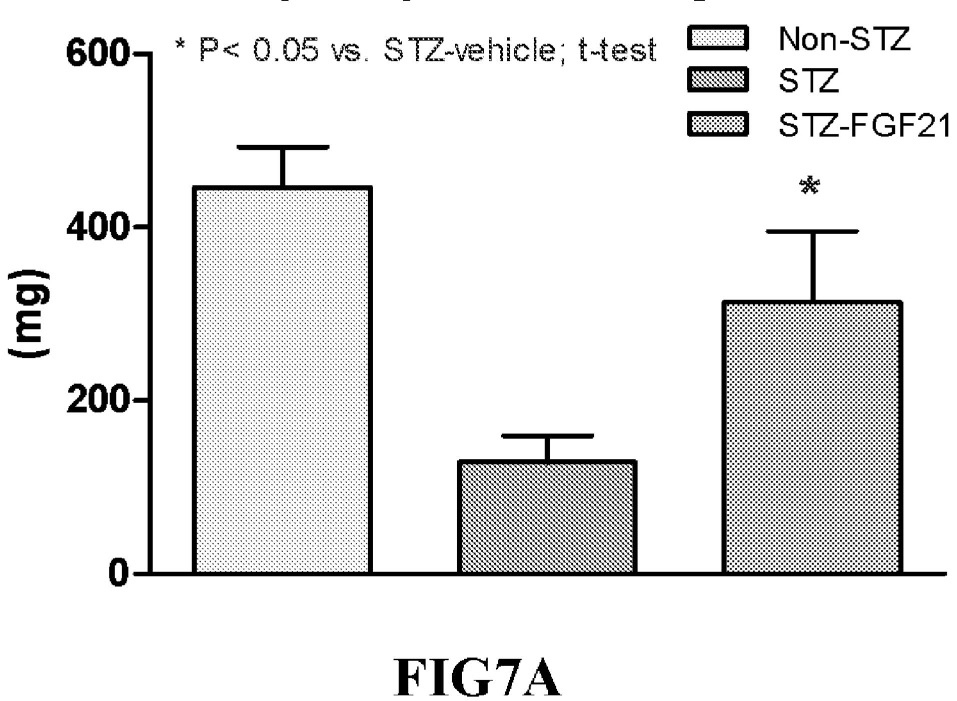
FIGS. 7A and 7B are graphical representations showing a change in epididymal fat weight when STZ mice are administered wild type FGF21 (FIG. 7A) and Variant 76 (referred to as Cmpd-A)(FIG. 7B). Wild type FGF21 (3 mg/kg, daily dose) reduced loss of fat tissue in STZ mice, and Variant 76 (1 or 3 mg/kg, 2 doses/week) reduced loss of fat tissue ketogenesis in STZ mice.
Figure 7B:
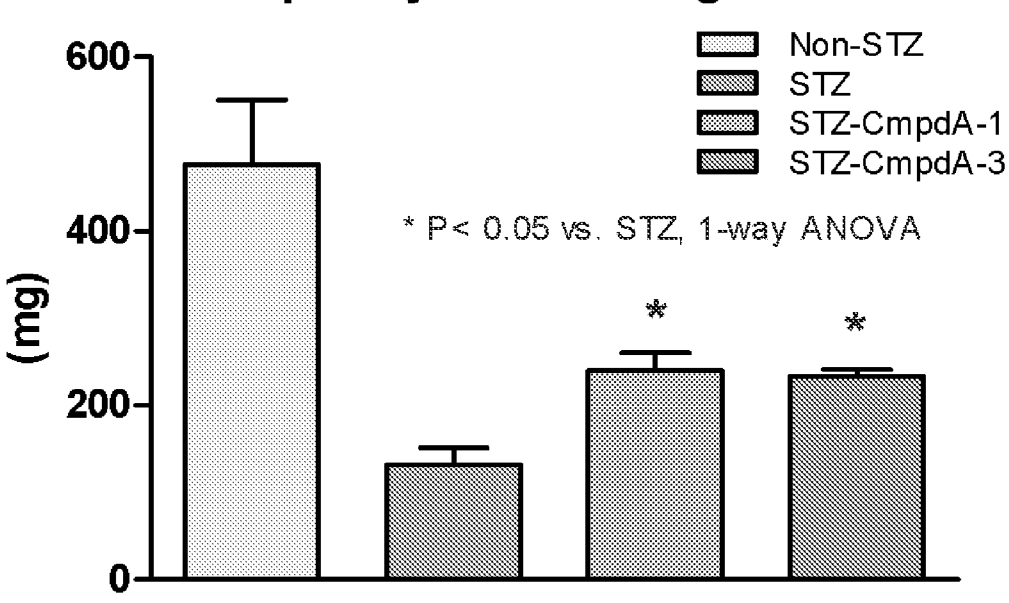

In seen in Tables 2 and 3 and FIGS. 1-7, the following were observed after administering wild type FGF21 and half-life-extended FGF21 (Variant 76): a decrease of hyperglycemia in STZ-induced T1D mice but without restoration of insulin secretion (FIG. 1 and Tables 2 and 3). Variant 76 also decreased HbA1c level during the study (FIG. 2). Both wild type FGF21 and Variant 76 increased carbohydrate utilization (as seen in FIG. 3) and energy expenditure (as seen in FIG. 4), reduced hyperphagia (as seen in FIG. 5), ketogenesis (as seen in FIG. 6) and loss of fat mass (as seen in FIG. 7).

TABLE 2

Body weight, glucose and insulin levels before (day 1) and after treatment (day 12) with wild type FGF21 at 3 mg/kg with daily dosing in Study 1.

| | Body weight (g) | | Glucose (mg/dl) | | Insulin (ng/ml) | |
|---|---|---|---|---|---|---|
| Group | day 1 | day 12 | day 1 | day 12 | day 1 | day 12 |
| Non-STZ | 27.9 ± 0.8 | 28.6 ± 0.7 | 216.8 ± 13.6 | 125.2 ± 0.9 | 3.02 ± 0.20 | 2.03 ± 0.52 |
| STZ | 27.8 ± 1.5 | 27.1 ± 1.4 | 548.0 ± 24.4 | 521.2 ± 35.5 | 0.92 ± 0.20 | 0.48 ± 0.16 |
| STZ-FGF21 | 26.7 ± 0.7 | 27.3 ± 0.9 | 540.3 ± 23.2 | 320.5 ± 69.3* | 0.95 ± 0.34 | 0.52 ± 0.14 |

Values are means ± SEM for n = 6 per group.
Glucose and insulin were measured in a fed condition.
*indicates $p < 0.05$ vs. STZ group by one-way ANOVA.

TABLE 3

Body weight, glucose and insulin levels before (day 1) and after treatment (day 26) with Variant 76 at 1 or 3 mg/kg with 2×/week dosing in Study 2.

| | Body weight (g) | | Glucose (mg/dl) | | Insulin (ng/ml) | |
|---|---|---|---|---|---|---|
| Group | day 1 | day 26 | day 1 | day 26 | day 1 | day 26 |
| Non-STZ | 32.5 ± 1.0 | 31.3 ± 0.9 | 164.8 ± 9.2 | 159.1 ± 5.8 | 1.96 ± 0.53 | 1.52 ± 0.30 |
| STZ | 28.6 ± 0.4 | 27.2 ± 0.5 | 452.3 ± 38.2 | 595.9 ± 69.7 | 0.49 ± 0.13 | 0.45 ± 0.06 |
| STZ-Cmpd A-1 | 29.0 ± 0.3 | 27.2 ± 0.5 | 453.1 ± 40.0 | 306.3 ± 62.4* | 0.44 ± 0.08 | 0.34 ± 0.05 |
| STZ-Cmpd A-3 | 29.0 ± 0.5 | 26.8 ± 0.3 | 452.1 ± 32.8 | 218.3 ± 13.3* | 0.66 ± 0.11 | 0.33 ± 0.04 |

Values are means ± SEM for n = 8 per group.
Glucose and insulin were measured in a fed condition.
*indicates $p < 0.05$ vs. STZ group by one-way ANOVA.

Example 2: Type B Insulin Resistance: FGF21 Stimulates Glucose Uptake in Human Adipocytes in the Presence of Anti-Insulin Receptor Monoclonal Antibody INSR knockout mice are not viable and typically die a few days after birth. While tissue specific knockout of INSR in mice is tolerated, the full spectrum of symptoms seen in patients with INSR mutation is not replicated in these animals. Thus, to further validate the clinical hypothesis that FGF21 can play a role in in the context of INSR inactivation, we simply measured the ability of FGF21 to promote glucose uptake in human adipocytes in the presence of a neutralizing anti-INSR antibody under conditions where insulin signaling is significantly impaired. This experiment effectively replicates the phenotype of Type-B insulin resistance (autoimmune insulin resistance), which is caused by development of neutralizing auto-antibodies to INSR.

Measurement of glucose uptake in differentiated human adipocytes is a widely used physiologically relevant readout. FGF21 exhibits glucose uptake in an insulin independent manner in human adipocytes. To study an INSR dysfunctional state in vitro, we tested the activity of insulin and FGF21 to stimulate glucose uptake in the absence and presence of an anti-INSR monoclonal antibody (Millipore Catalogue #MAB1137).

Primary human adipocytes were seeded in a 96-well collagen coated plate at 15,000 cells/well, differentiated in adipocyte differentiation media (Cell Application) for 12 days, and then treated for 3 days with adipocyte maintenance media (Cell Application). For glucose uptake measurement, adipocytes were treated with 100 nM insulin for 30-min or 100 nM FGF21 for 24 h at 37° C. Adipocytes were washed with Krebs ringer phosphate (KRP) buffer and treated with KRP containing 0.05 μCi of 2-deoxy-D-[3H] glucose (2-DOG) for 1 hr at 37° C. Cells were lysed and glucose uptake measured using MicroBeta counter (Perkin Elmer). To study the glucose uptake of insulin or FGF21 in the presence of anti-INSR antibody, the adipocytes were pre-treated with 0.1 nM, 10 nM, and 100 nM of antibody for 1 h at 37° C. prior to insulin or FGF21 treatment.

Figure 8A:
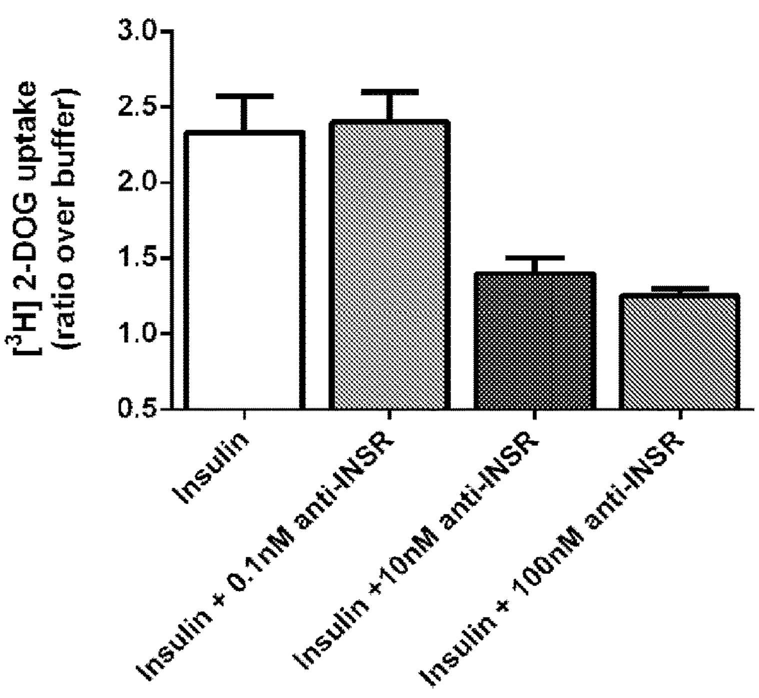
FIGS. 8A and 8B show that blockade of Insulin Receptor (INSR) via administration of inhibitory monoclonal antibody against the insulin receptor completely blocks insulin dependent glucose uptake by differentiated human adipocytes in the presence of excess insulin (100 nM) (FIG. 8A); however 100 nM FGF21 is still able to promote glucose uptake in the presence of up to 10 nM anti-INSR Ab (FIG. 8B), demonstrating that an FGF21 therapy may be beneficial in Type-B insulin resistance (autoimmune insulin resistance), and by extension may also promote insulin independent glucose uptake in the presence of a generally defective (i.e., mutated) insulin receptor.
Figure 8B:
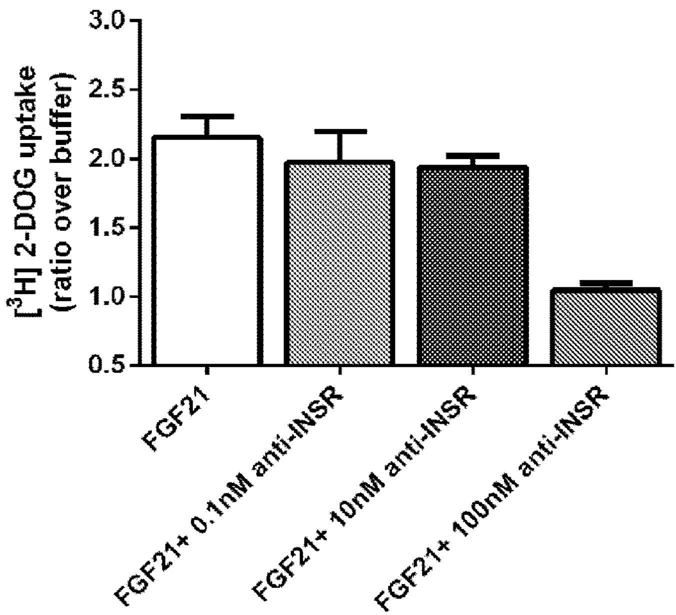

As shown in FIG. 8A, 100 nM insulin on its own stimulated a robust glucose uptake response in human adipocytes. In the presence of 0.1 nM anti-INSR antibody, insulin-stimulated glucose uptake was unaltered. However, pre-treatment with 10 nM and 100 nM of anti-INSR antibody abolished insulin stimulated glucose uptake. However as shown in FIG. 8B, 100 nM FGF21 stimulated glucose uptake in the absence of anti-INSR antibody. Pre-treatment with anti-INSR antibody at 0.1 nM and 10 nM did not significantly reduce (10% and 12% respectively) FGF21 stimulate glucose uptake. FGF21 activity was only abolished in the presence at high concentration of anti-INSR antibody, administered at 100 nM.

These data support use of an FGF21 analog in patients with Type B insulin resistance (autoimmune insulin resistance) as well as any with other insulin receptor deficiencies (e.g., caused by mutations in the insulin receptor, such as Type A insulin resistance, Rabson Mendonhall Syndrome and Donohue Syndrome).

Example 3: HIV HAART Induced Partial Lipodystrophy

To study the effect of FGF21 in a model of lipodystrophy induced by HIV highly active antiretroviral therapy (HAART), 12-week-old C57BL mice (Taconic) were provided with PicoLab mouse diet #5058 (10% fat content) formulated by Research Diets with 0.1 or 0.2% HIV protease inhibitor Ritonavir. After 50 days of Ritonavir treatment, mice developed lipodystrophy and were divided into two subgroups, receiving either FGF21 V76 (5 mpk, s.c.) or PBS vehicle 2×/wk for 4 wks. Body weight, % body fat mass, plasma glucose, insulin and TG were measured during the study. Oral glucose tolerance test (OGTT) was assessed on treatment day 23. Liver lipid content was measured at the termination of the study.

Figure 9A:
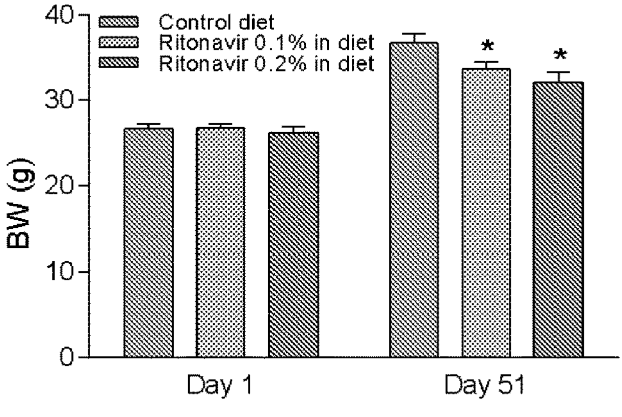
FIGS. 9A-C demonstrates the effect of HIV protease inhibitor Ritonavir treatment on body weight gain, body fat gain, and plasma triglycerides, respectively, in mice.
Figure 9B:
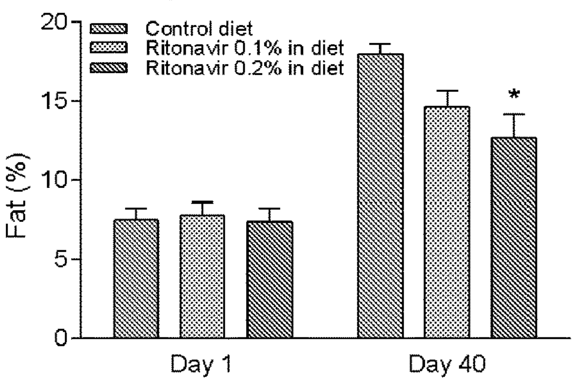
Figure 9C:

Prior to V76 treatment, mice on diet mixed with Ritonavir developed a significant reduction in body weight gain (FIG. 9A) and fat content (FIG. 9B), as well as increased plasma triglyceride levels (FIG. 9C) relative to mice on control diet.

Figure 10A:
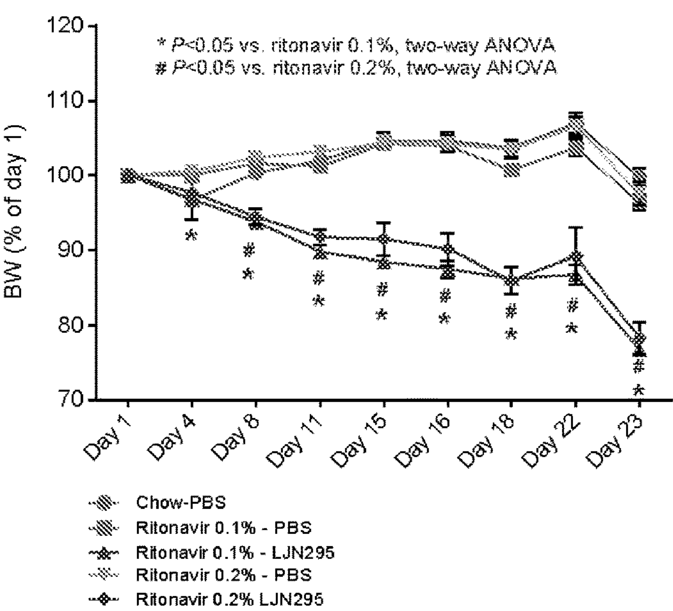
FIGS. 10A-E demonstrates the effect of Ritonavir with or without FGF21 v76 according to the following readouts: body weight (FIG. 10A); white adipose tissue (WAT) weight (FIG. 10B); plasma glucose (during an oral glucose tolerance test (OGTT))(FIG. 10C); Homeostatic Model Assessment of Insulin Resistance (HOMA-IR)(FIG. 10D); and liver lipid content (FIG. 10E), in all cases in mice already treated for 51 days with Ritonavir to induce disease state, and then treated for 23 days with both FGF21 and Ritonavir to treat the same, compared to chow fed PBS treated control mice.
Figure 10B:
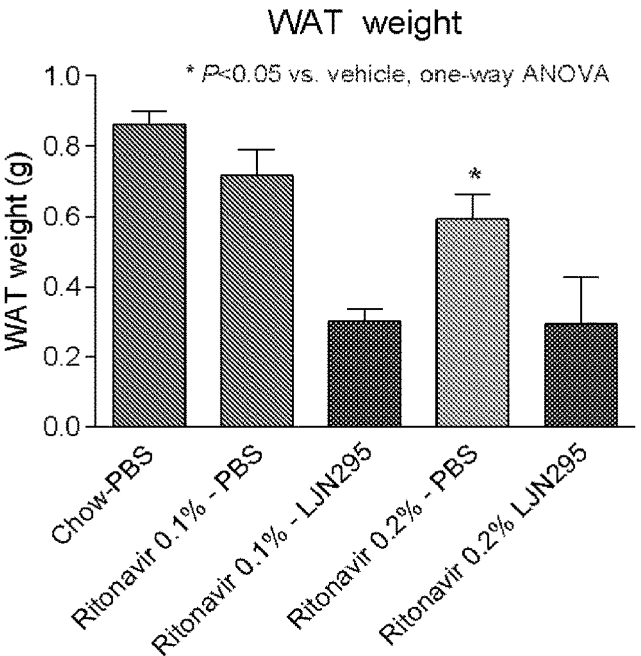
Figure 10C:
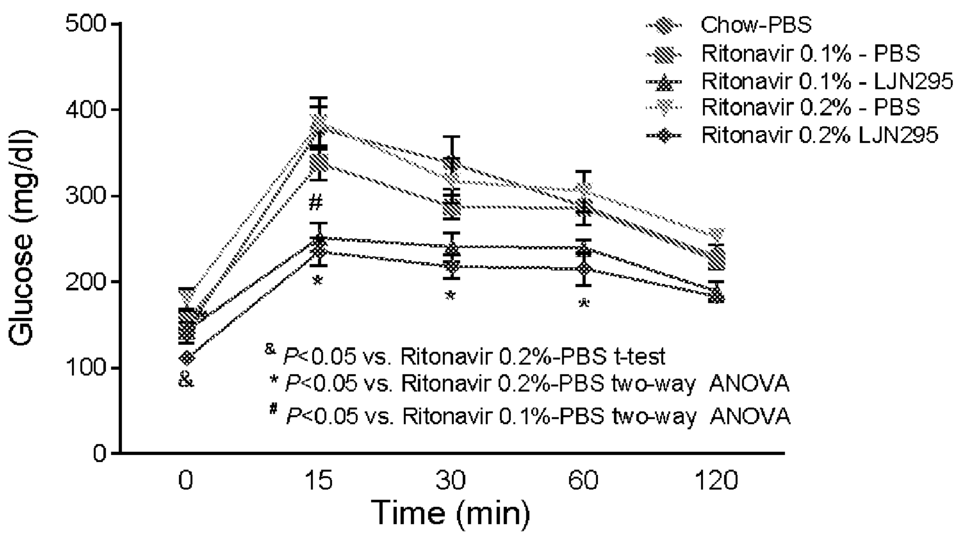
Figure 10D:
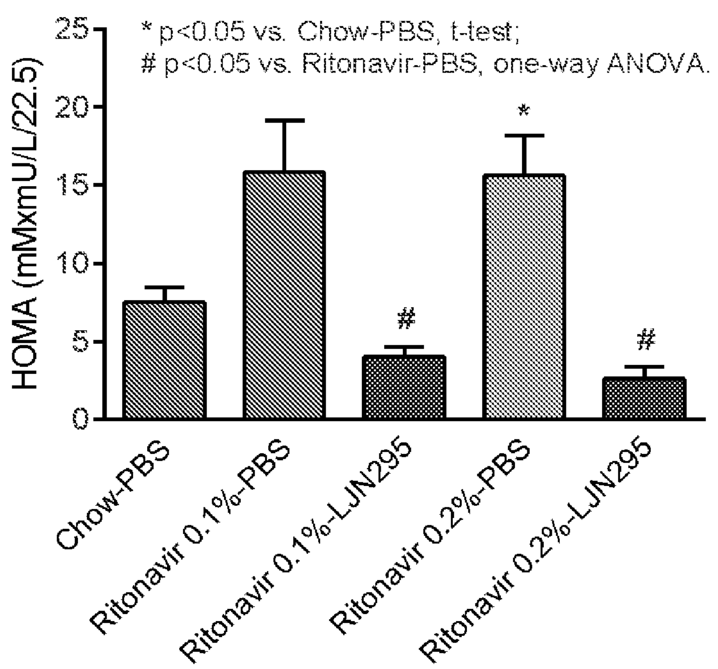
Figure 10E:
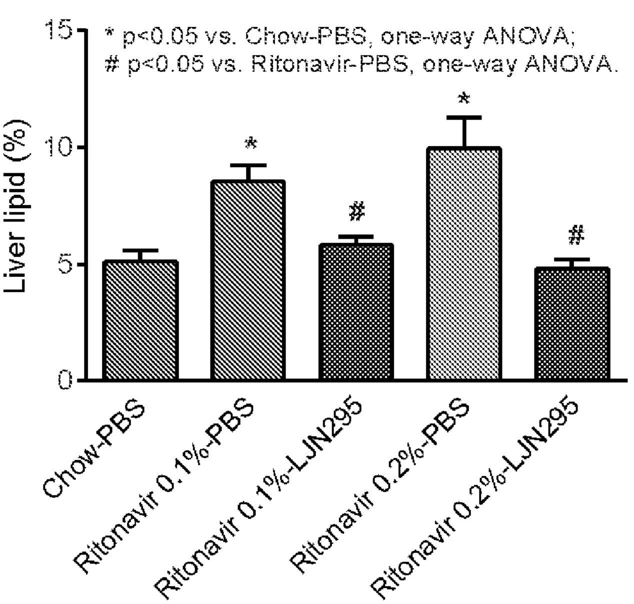

Body weight was significantly reduced with FGF21 v76 treatment (FIG. 10A). Fat mass was also significantly reduced with FGF21 v76 treatment (FIG. 10B). Mice treated with FGF21 v76 had significantly improved glucose excursion during OGTT (FIG. 10C). Ritonavir treatment resulted in increased HOMA-IR and liver lipid content. Treatment with FGF21 v76 completely normalized HOMA-IR (FIG. 10D) and liver steatosis (FIG. 10E) in both 0.1 and 0.2% Ritonavir groups.

In the HIV HAART-induced partial lipodystrophy mouse model, treatment with FGF21 v76 for 25 days (5 mpk, 2×/wk) completely alleviated insulin resistance and liver steatosis induced by 75 days of diet mixture with Ritonavir. The preclinical data support a novel approach of FGF21 therapy in patients developed lipodystrophy by HIV protease inhibitors.

Example 4: t10, c12 Conjugated Linoleic Acid Induced Lipodystrophy

To study the effects of FGF21 V101 in a second more severe lipodystrophy model, mice were fed a diet containing 0.6% t10, c12 conjugated linoleic acid (t10, c12 CLA). Mice were treated with FGF21 V101 starting either 1) one week after diet initiation ("Prevention" mode) or 2) three weeks after diet initiation ("Reversal" mode). The effects of recombinant murine leptin were also tested as a positive control in the "Reversal" mode. Body weight, liver fat, adipose mass, glucose, insulin and plasma lipids were the primary readouts.

Animals:

C57B6J male mice were housed individually and acclimated to facility for 6 weeks on normal chow prior to starting special diets at 18 weeks of age. The mice were grouped into categories listed in Table 5, below.

Diets:

Purified, 110, c 12 CLA was synthesized by Matreya, LLC and delivered to Research Diets, Inc. Purified custom diets will be prepared fresh weekly by Research Diets, Inc. The t10, c12 CLA diet contained 0.6% t10, c12 CLA. Daily rations were bagged, purged with Nitrogen, vacuum-sealed, stored at −20° C. and served daily to the mice. Diet ingredients are itemized in Table 4 below.

TABLE 4

| | t10, c12 CLA diet | | Control Diet | |
|---|---|---|---|---|
| | gm | kcal | gm | kcal |
| % | | | | |
| Protein | 18.5 | 19.2 | 18.5 | 19.2 |
| Carbohydrate | 67.3 | 70.9 | 67.3 | 70.9 |
| Fat | 4.3 | 10.0 | 4.3 | 10.0 |
| Total | | 100.0 | | 100.0 |
| kcal/gm | 3.85 | | 3.85 | |
| Ingredient | | | | |
| Casein | 192 | 768 | 192 | 768 |
| L-Cystine | 3 | 12 | 3 | 12 |
| Corn Starch | 325 | 1300 | 325 | 1300 |
| Maltodextrin | 35 | 140 | 35 | 140 |
| Sucrose | 350 | 1400 | 350 | 1400 |
| Cellulose | 48.7 | | 48.7 | |
| t10, c12 CLA | 6 | 54 | | 0 |
| Sunflower Oil | 39 | 351 | 45 | 405 |
| Mineral Mix S10026 | 10 | | 10 | |
| DiCalcium Phosphate | 13 | | 13 | |
| Calcium Carbonate | 6 | | 6 | |
| Potassium Citrate, 1 H2O | 17 | | 17 | |
| Vitamin Mix V10001 | 10 | 40 | 10 | 40 |
| Choline Bitartrate | 2 | | 2 | |
| Total | 1056 | 4065 | 1056 | 4065 |

After 2 week acclimation to facility mice were switched to 0.6% t10, c12 CLA diet or the control diet. One group of chow-fed mice (GROUP 11 (see Table 4 for the specifics of this and the other groups)) was sacrificed at study start for day zero measurements of liver fat and adipose mass. In addition, a group of mice on the t10, c12 CLA diet (GROUP 9) and a group of mice on the control diet (GROUP 10) were sacrificed after one week on diet and also after three weeks of diet (GROUPS 7 and 8) without any additional treatments. Data for groups 7-10 are used to establish liver fat and adipose mass prior to FGF21 v101 or leptin treatment. Another group (GROUP 6) were maintained on the control diet until study end to serve as a normal control for study endpoints.

One group of mice (GROUP 1) started FGF21 v101 treatment after one week on the t10, c12 CLA diet to access whether FGF21 can "prevent" the lipodystrophic progression. Another group of mice (GROUP 2) started FGF21 v101 treatment after three weeks on the t10, c12 CLA diet to access whether FGF21 v101 could "reverse" the disease. The control group for FGF21 v101 (GROUP 3) received PBS injections starting after three weeks on the t10, c12 CLA diet. Thereafter GROUPS 1-3 received subcutaneous injections of PBS or FGF21 once per week. After three weeks on diet, GROUP 4 and 5 were implanted subcutaneously with Alzet osmotic minipumps to continuously deliver Leptin or saline, respectively. Thereafter, body weight, blood glucose, plasma insulin and plasma lipids (tail bleed) were measured weekly for GROUPS 1-5.

After five weeks on diet, GROUPS 1-6 received an oral glucose tolerance test (OGTT) (2 g glucose per kg) with glucose measured 0, 10, 20, 40 and 90 min after glucose challenge. After six weeks on diet, body weight, blood glucose, plasma insulin and plasma lipid (tail bleed) were measured for GROUPS 1-6 prior to sacrifice. Liver, adipose depots (epidydimal, retroperitoneal, and inguinal), muscle (soleus and TA) and blood for plasma (cardiac stick) were collected at sacrifice. Liver and adipose depots were weighed. Liver and muscle tissues was analyzed for fat content using a Bruker mini spectrophotometer. Total liver fat (g) is calculated as (liver weight×(% liver fat/100)).

Dose Administration:

FGF21 V101 was provided as a solution in PBS. 1 mg/kg administered subcutaneously once per week (using a 0.25 mg/ml solution of FGF21 V101).

Murine Leptin from Sigma, Cat #L3772, Lot #081M1287V, recombinant expressed in *E. coli*. lyophilized powder dissolved in PBS, was administered at 1 mg/kg/d dosage via continuous subcutaneous infusion via Alzet osmotic minipump.

TABLE 5

| Study Mice |
|---|
| GROUP 1 = FGF21 prevention (n = 10) |
| GROUP 2 = FGF21 reversal (n = 10) |
| GROUP 3 = Vehicle Injection (n = 10) |
| GROUP 4 = Leptin Pump (n = 10) |
| GROUP 5 = Vehicle Pump (n = 10) |
| GROUP 6 = Control diet for study end (n = 10) |
| GROUP 7 = 3 week CLA time zero (n = 7) |
| GROUP 8 = 3 week Control time zero (n = 7) |
| GROUP 9 = 1 week CLA time zero (n = 7) |
| GROUP 10 = 1 week Control time zero (n = 7) |
| GROUP 11 = chow fed mice (n = 5) |

Adipose Depots

Figure 11A:
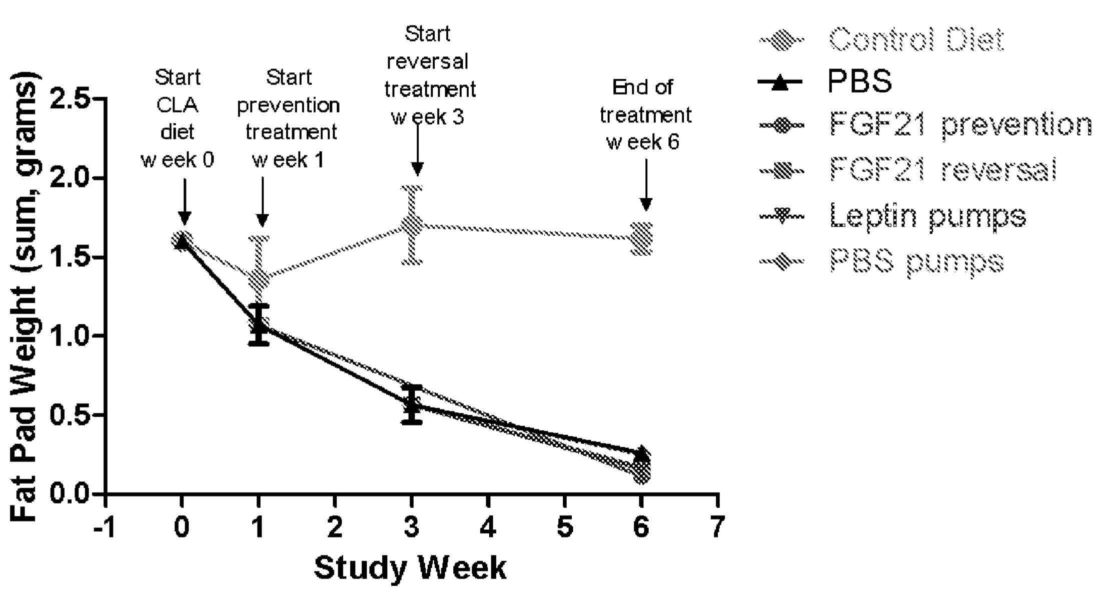
FIGS. 11A and B profile the effect of 0.6% t10, c12 conjugated linoleic acid (t10, c12 CLA) in the diet of mice on fat pad weight (which is thought to induce lipodystrophy, as explained in greater detail below) vs chow diet as a function of time.
Figure 11B:
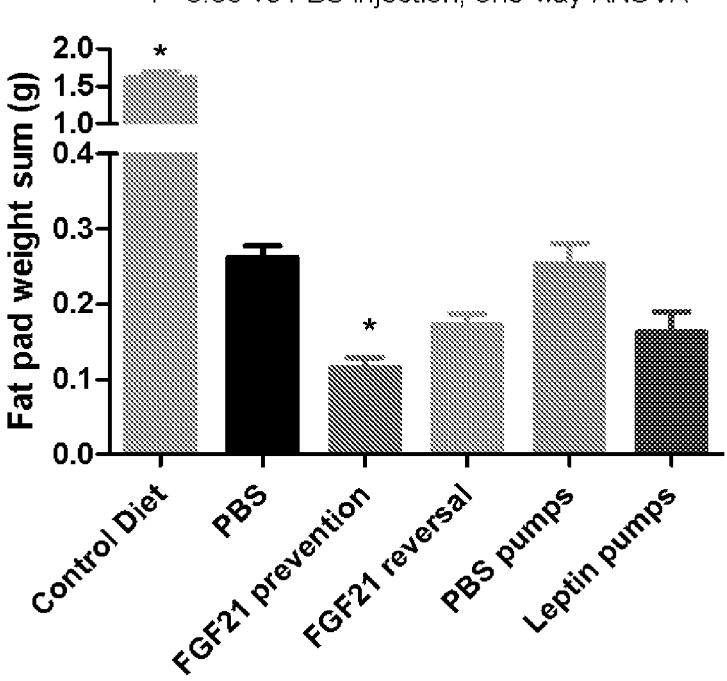
FIG. 11B shows said effect at the end of the study.

The time course of loss in adipose mass is depicted in FIG. 11A. The weight of adipose depots (FIG. 11B) was measured as the sum of epidydimal, retroperitoneal and subcutaneous inguinal fat. These three depots were the only substantial depots detected since we used normal mice which were fed a diet with a low fat content (10% kcal from fat). Mice fed t10, c12 CLA diet (and treated with PBS) lost approximately 85% of their adipose mass during the six week study as compared to mice on Control Diet (1.6 g for Control diet versus 0.27 g for CLA diet).

In the "prevention" mode, mice treated with FGF21 v101 lost an additional 0.15 g adipose mass (P<0.05 by one-way ANOVA). In the "reversal" mode, mice treated with FGF21 v101 lost an additional 0.1 g adipose mass (not statistically significant). Similarly mice treated with leptin lost an additional 0.1 g adipose mass (not statistically significant). As expected, neither FGF21 v101 nor leptin treatment restored peripheral fat mass.

Liver Fat

Figure 12A:
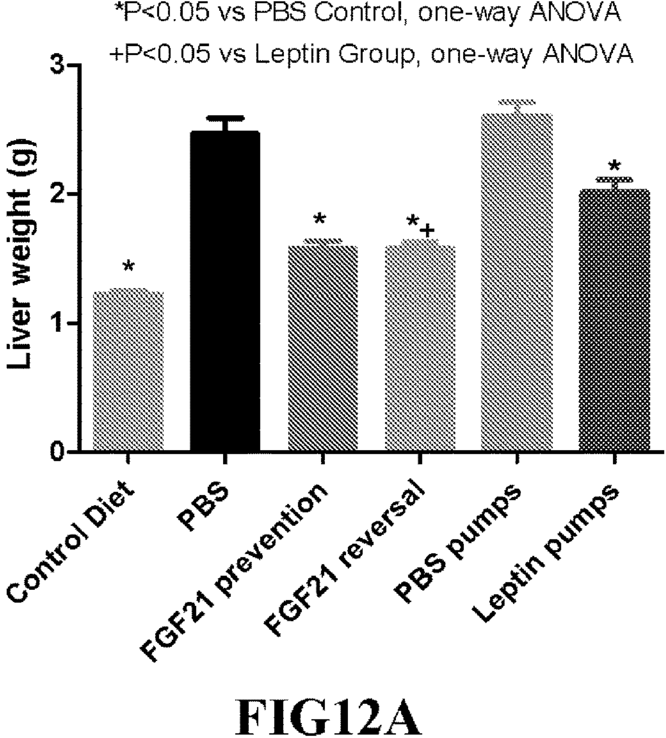
FIGS. 12A-D show that FGF21 (v101), administered in either "prevention" or "treatment" modes (terms described herein), and leptin administered in treatment mode, all reverse the increase in liver weight (FIG. 12A), increase in liver fat content (FIG. 12B), hyperglycemia (FIG. 12C), and hyperinsulinemia (FIG. 12D), respectively, as induced by a 0.6% t10, c12 conjugated linoleic acid (t10, c12 CLA) in the diet of mice.
Figure 12B:
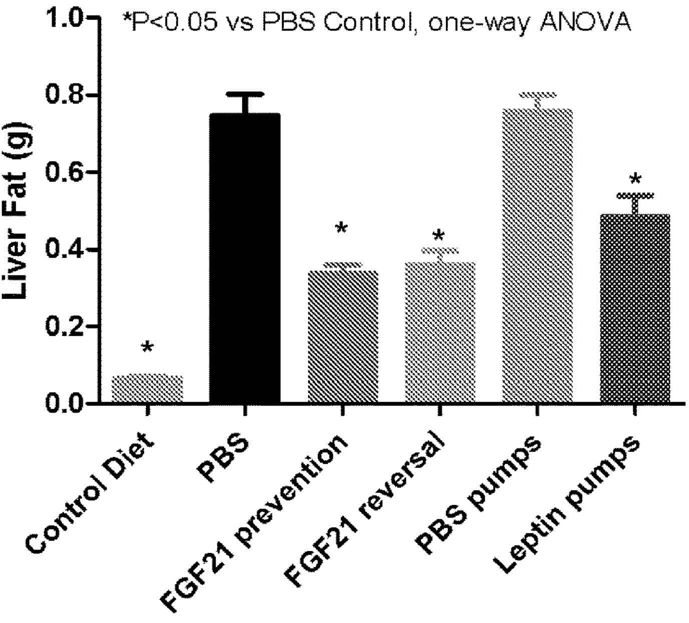

At time of sacrifice, the weight of the liver was measured (FIG. 12A). Small pieces of liver (approximately 40 mg) were sampled for measurement of percent liver fat using a Bruker minispectrophomoter tissue composition analyzer. Total liver fat (g) was calculated as (liver weight×(% liver fat/100)) (FIG. 12B). Mice fed t10, c12 CLA diet (and treated with PBS), accumulated 12-fold more fat in their livers during the six week study as compared to mice on Control Diet (0.06 g for Control diet versus 0.75 g for CLA diet, P<0.05 by one-way ANOVA). Liver fat accumulation was reduced to half in mice treated with FGF21 (0.75 g for PBS treated group, 0.34 g for FGF21 v101 "prevention" group, 0.36 g for FGF21 v101 "reversal" group.) Similarly, liver fat accumulation was reduced in mice treated with leptin. (0.75 g for PBS treated group, 0.48 g for leptin group.) All reductions in liver fat were statistically significant versus PBS-treated groups (P<0.05 by one-way ANOVA). The reduction in FGF21-treated groups was not significantly different from the reduction in the leptin-treated groups.

Fed Blood Glucose and Plasma Insulin

At week 6 of the study, mice fed t10, c12 CLA diet and treated with PBS, had a 40% increase in fed blood glucose (P<0.05 by one-way ANOVA) and a 20-fold increase in fed plasma insulin (p<0.05 by one-way ANOVA) consistent with significant insulin resistance and impaired glucose tolerance induced by the t10, c12 CLA diet and lipodystrophy.

Figure 12C:
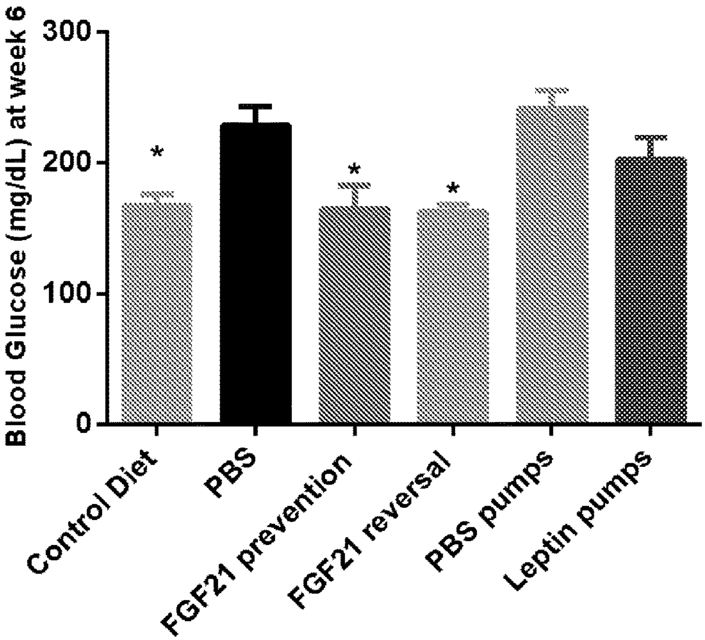

However, blood glucose was not elevated in mice on the CLA diet treated with FGF21 v101, in either the "treatment" or "prevention" modes. Blood glucose was partially elevated in mice on the CLA diet who were treated with leptin (230 mg/dL for PBS-treated group on CLA diet, 165 mg/dL for FGF21 "prevention" group on CLA diet, 163 mg/dL for FGF21 "reversal" group on CLA diet, 203 mg/dL for leptin group on CLA diet, 167 mg/dL for mice on Control diet) (FIG. 12C).

Figure 12D:
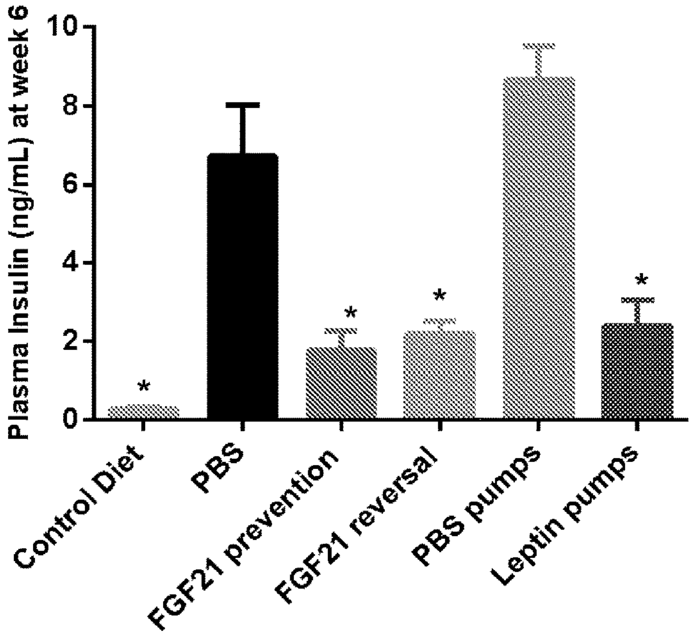

Similarly, the increase in plasma insulin was markedly blunted in mice on the CLA diet who were treated with FGF21, in both the "treatment" or "prevention" modes and in mice treated with leptin (6.7-8.7 ng/mL for PBS-treated groups on CLA diet, 1.8 ng/ml for FGF21 "prevention" group on CLA diet, 2.2 ng/ml for FGF21 "reversal" group on CLA diet, 2.4 ng/ml for leptin group on CLA diet, 0.3 ng/ml for mice on Control diet)(FIG. 12D).

Taken together, the elevation in blood glucose and plasma insulin that resulted from CLA diet, indicates that CLA promoted insulin resistance. The reduction in blood glucose and plasma insulin in mice on CLA diet which resulted from treatment with FGF21 (in both the "treatment" or "prevention") and treatment with leptin, indicates that these treatments prevented and/or reversed the CLA-induced insulin resistance.

Oral Glucose Tolerance Test

At week 5 of the study, an OGTT was performed after a 5 h fast. Mice were dosed orally with glucose (2 g/kg, 8 ml/kg). Blood glucose was measured before the glucose dose and 10, 20, 40 and 90 min after the glucose dose and the blood glucose AUC 0-90 was calculated (FIG. 12E).

The blood glucose AUC 0-90 was 30% higher in mice fed t10, c12 CLA diet (treated with PBS) as compared to mice fed the Control diet. Blood glucose AUC in control mice and mice on the CLA diet who were treated with FGF21, in either the "treatment" or "prevention" modes was reduced compared to the PBS treated group on the CLA diet.

Summary

FGF21 V101 (1 mg/kg/wk) prevented and reversed liver lipid accumulation and insulin resistance in a lipodystrophy model using mice fed 0.6% t10, c12 conjugated linoleic acid. These data suggest that and FGF21 analog could be useful for treatment of insulin resistance and/or hyperglycemia induced by significant fat loss (lipodystrophy).

Example 5: Effect of FGF21 Fusion Protein V103 in a Lipodystrophy Mouse Model

Methods

Animals

Twenty-week old male C57BL mice (Taconic, Germantown, NY) were housed four per cage in a normal light cycle room (light on from 6:00 a.m. to 6:00 p.m.) and given access to food and water ad libitum. Lipodystrophy was induced by feeding mice a specially formulated diet containing ritonavir (0.2% w/w) in PicoLab Mouse Diet 20 #5058 (21.6% kcal from fat). The mice in a control group were given Diet 20 #5058 without ritonavir. When the mice on ritonavir diet became lipodystrophic (defined by increased plasma triglyceride level and weight loss at day 50 on the diet), they received either PBS (phosphate buffered saline) vehicle or FGF21 fusion protein V103, as described herein, (1 mg/kg, subcutaneous injection) for a total of 3 injections given on days 1, 8 and 17 of the treatment. Mice not on the ritonavir diet were also injected with PBS during the study. The total treatment length of the study was 25 days.

Experiments were conducted under an approved Institutional Animal Care and Use Committee protocol 12CVM043. All procedures in this study were in compliance with the Animal Welfare Act Regulations 9 CFR Parts 1, 2 and 3, and other guidelines.

Measurements

Body weight and food intake were measured throughout the study. Plasma glucose, insulin, triglyceride (TG) and free fatty acid (FFA) concentrations were measured in a fed or fasted condition. An insulin facilitated glucose tolerance test (IFGTT, with an intraperitoneal (i.p.) injection of a mixture of glucose at 1 g/kg and insulin at 0.5 U/kg) was given on day 17 after 5 hours of fast. Plasma glucose levels were measured before and during the IFGTT. An oral glucose tolerance test (OGTT, with an oral dose of glucose at 1 g/kg) was given on day 24 after an overnight fast. Plasma glucose and insulin levels were measured before and during the OGTT. Body composition was determined with Echo MRI before and after the ritonavir diet induction, and at the end of V103 treatment (on day 24). At the termination of the study, liver, epididymal fat and inguinal fat were collected and weighed. Liver and soleus muscle collected at the end of the study were analyzed for tissue lipid content.

Glucose was measured using a glucose meter (Embrace, Omnis Health, Natick, MA). Insulin was measured using an ultra-sensitive mouse insulin enzyme-linked immunosorbent assay (ELISA) kit (Crystal Chem, Inc., Chicago, IL, cat #90080). TG and FFA were measured using a highly sensitive fluorescent assay based on the horseradish peroxidase catalyzed oxidation of Amplex® Red by hydrogen peroxide to resorufin. Body composition was measured using EchoMRI-100 (Echo Medical Systems, Huston, TX). Liver and muscle lipid content was measured using NMR Mq-60 tissue fat analyzer (BRUKER Optics Inc., The Woodlands. TX).

Data Analysis

Statistical analysis was performed using GraphPad Prism 5.0 (GraphPad Software, San Diego, CA). Time course analysis was performed by a two-way analysis of variance (ANOVA) followed by a post-hoc test using Bonferroni's method for each time point. Analysis among the three groups without time course was conducted using a one-way ANOVA followed by Dunnett's test. Analysis between the two ritonavir groups was also performed using a non-paired and two-tailed Student t-test. Data are presented as mean±standard error of the mean (SEM). The level of statistical significance was set at $p<0.05$.

Results

Effect of Ritonavir on Body Weight and Percent Fat Mass

Mice treated with Ritonavir for 8 weeks show a significant body weight loss and mild reduction in fat mass in. Due to a high fat content in both control and ritonavir diets, fat mass was more than doubled in both diet groups at the end of the diet treatment.

Effect of Ritonavir on Plasma Lipids, Glucose and Insulin

Following the Ritonavir diet, there was a significant increase in both plasma triglycerides (TG) and free fatty acids (FFA). Plasma glucose and insulin were not affected by Ritonavir treatment; however, insulin levels in both groups were much higher on day 50 compared to the values on day 1, suggesting that the high fat content of the diets led to insulin resistance in both groups.

Effect of V103 on Body Weight and Percent Fat Mass

Treatment with V103 significantly reduced body weight (BW) and percent fat mass. Food intake was not affected by the treatment (data not shown). Body weight was measured during the V103 treatment, and percent fat mass was measured at the end of the treatment (day 24). V103 treatment led to a significant weight loss as well as a reduction in fat mass. #$p<0.05$ by a two-way ANOVA compared to the Control-Vehicle group; *$p<0.05$ by a two-way ANOVA (BW) or a one-way ANOVA (fat mass) compared to the Ritonavir-Vehicle group.

Effect of V103 on Plasma Lipids, Glucose and Insulin

Treatment with V103 led to a significant reduction in plasma TG and FFA in Ritonavir-treated mice to the levels similar to those seen in the control diet group. Both plasma glucose and insulin were significantly reduced in mice treated with V103. The insulin level in the control diet group was elevated during the study, indicating insulin resistance as a result of a high diet fat content. In mice feed a standard chow diet, plasma insulin concentration is normally around 1 ng/ml (RD-2005-50000).

Data are mean±SEM. N=7-8 per group. Plasma TG and FFA were measured in a fed condition at the end of the treatment (day 25). V103 treatment significantly reduced plasma TG and FFA levels. #$p<0.05$ by a one-way ANOVA compared to the Control-Vehicle group; *$p<0.05$ by a one-way ANOVA compared to the Ritonavir-Vehicle group.

Data are mean±SEM. N=7-8 per group. Plasma glucose and insulin were measured in a fed condition during the V103 treatment. V103 treatment significantly reduced both plasma glucose and insulin. #$p<0.05$ by a two-way ANOVA compared to the Control-Vehicle group; *$p<0.05$ by a two-way ANOVA compared to the Ritonavir-Vehicle group.

Effect of V103 on Insulin Sensitivity and Glucose Utilization

Insulin sensitivity and glucose utilization were assessed using an IFGTT on day 17 and an OGTT on day 24. V103 treatment led to significant improvement in insulin sensitivity as indicated by a much suppressed glucose excursion during the IFGTT, during which exogenous insulin together with glucose were administered. Data are mean±SEM. N=7-8 per group. Plasma glucose was measured in a fasted condition during the IFGTT. Glucose levels in V103 treated group were significantly lower than the vehicle treated mice. *$p<0.05$ by a two-way ANOVA compared to the Ritonavir-Vehicle group.

Similarly, treatment with V103 significantly improved glucose tolerance during an OGTT in both plasma glucose and insulin. Data are mean±SEM. N=7-8 per group. Plasma glucose and insulin were measured in a fasted condition during the OGTT. Both glucose and insulin levels in V103 treated group were significantly lower than the vehicle treated mice. *$p<0.05$ by a two-way ANOVA compared to the Ritonavir-Vehicle group.

In addition, HOMA-IR (homeostasis model of assessment—insulin resistance, calculated based on fasting glucose and insulin levels) was significantly improved in mice treated with V103. Thus, V103 was highly efficacious on improving insulin sensitivity in ritonavir treated mice. Data are mean±SEM. N=7-8 per group. Fasting plasma glucose and insulin were measured on day 24 following an overnight fast. HOMA-IR in V103 treated group was significantly lower than the vehicle treated mice. *$p<0.05$ by a one-way ANOVA compared to the Ritonavir-Vehicle group.

Effect of V103 on Liver and Muscle Lipid Content and Tissue Weight

V103 treatment resulted in a significantly reduction of lipid content in both liver and muscle. Data are mean±SEM.

N=7-8 per group. Lipid content of liver and soleus were measured at the end of the treatment (day 25). V103 treatment significantly reduced lipid content in both liver and soleus muscle. Lipid content in soleus muscle was also low in the Ritonavir-Vehicle group. #$p<0.05$ by a one-way ANOVA compared to the Control-Vehicle group; *$p<0.05$ by a one-way ANOVA (liver lipid content) or Student t-test (soleus lipid content) compared to the Ritonavir-Vehicle group.

Ritonavir treatment resulted in lipoatrophy with an increased liver mass. Liver weight was significantly increased while white adipose pad weight was decreased with Ritonavir treatment. V103 treatment resulted in a normalization of liver weight but a further reduction of adipose pad weight.

Data are mean±SEM. N=7-8 per group. Tissue weight of liver, epididymal fat and inguinal fat were measured at the end of the treatment (day 25). As indicated, tissue weight was significantly increased in the liver but decreased in epididymal fat in the Ritonavir-Vehicle group, and V103 treatment significantly reduced weight of all three tissues. #$p<0.05$ by a one-way ANOVA compared to the Control-Vehicle group; *$p<0.05$ by a one-way ANOVA compared to the Ritonavir-Vehicle group.

Plasma Levels of V103 During the Study

Plasma levels of V103 were measured acutely after the first dose (4 and 24 hours post dose) and chronically after the second (9 days after the dose) and third (8 days after the dose) doses. Plasma levels of V103 were well maintained during the study. Data are mean±SEM. N=8 per group. Plasma V103 levels were measured at 4 and 24 hours after the first dose, 9 days after the second dose and 8 days after the third dose.

Discussion

We evaluated the effect of V103 in an HIV proteinase inhibitor-induced lipodystrophy mouse model. With a chronic daily treatment of ritonavir provided in diet, mice developed lipodystrophy conditions, such as increased plasma TG and FFA levels, increased liver lipid content, and reduced fat mass and body weight. Since lean mice on a standard chow diet maintain a low fat mass and body weight, in order to provide a sufficient amount of fat for redistributing from adipose tissue to the liver with ritonavir treatment, Diet 20 #5058 was used with or without (for the control group) addition of ritonavir. The diet, which has been used for mouse breeding purpose, contains double amount of fat compared to a standard chow diet. A disadvantage of using this diet is that it may cause insulin resistance due to its high fat content. Indeed, in this study we observed an increase in plasma insulin level and percent body fat mass in the control diet fed mice.

Treatment with V103 for just three doses in 25 days effectively improved dyslipidemic condition with significantly reduced plasma TG and FFA levels as well as lipid content in the liver and muscle. In addition, V103 treatment significantly enhanced insulin sensitivity and glucose utilization as illustrated by a suppression of glucose excursion during both IFGTT and OGTT as well as an improved HOMA-IR.

The results from this study demonstrated that V103 can provide a therapeutic approach for treating patients with lipodystrophy. The profound effect of V103 on weight loss and lipid reduction suggests its valuable potential for treating obesity and fatty liver diseases.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. A method of treating HIV-HAART induced partial lipodystrophy comprising administering to a subject in need thereof a therapeutically effective amount of an FGF21 protein variant Fc fusion protein comprising amino acid sequence SEQ ID NO: 5.

2. The method of claim 1, wherein the administration is subcutaneous.

3. The method of claim 1, wherein the administration comprises a dose of about 0.1 μg/kg to about 100 mg/kg.

4. The method of claim 3, wherein the administration comprises a dose of about 1 μg/kg up to about 100 mg/kg.

5. The method of claim 1, wherein the administration is about twice per week to about once per week.

6. The method of claim 5, wherein the administration is about once per week.

7. The method of claim 6, wherein the administration is about once per week with a dose of about 0.7 mg up to about 700 mg.

8. The method of claim 1, wherein the subject is undergoing antiretroviral therapy (ART).

9. The method of claim 8, wherein the antiretroviral therapy (ART) comprises an HIV protease inhibitor.

10. The method of claim 1, further comprising administering one or more additional therapeutic agents.

11. A method of treating HIV-HAART induced partial lipodystrophy comprising administering to a subject in need thereof a therapeutically effective amount of an FGF21 protein variant Fc fusion protein, wherein the FGF21 protein variant Fc fusion protein is administered in the form of a pharmaceutical composition comprising a therapeutically effective amount of the FGF21 protein variant Fc fusion protein in admixture with a pharmaceutically or physiologically acceptable formulation agent selected for suitability with the mode of administration, and wherein the FGF21 protein variant Fc fusion protein comprises amino acid sequence SEQ ID NO: 5.

12. The method of claim 11, wherein the administration is subcutaneous.

13. The method of claim 11, wherein the administration comprises a dose of about 0.1 μg/kg to about 100 mg/kg.

14. The method of claim 13, wherein the administration comprises a dose of about 1 μg/kg up to about 100 mg/kg.

15. The method of claim 11, wherein the administration is about twice per week to about once per week.

16. The method of claim 15, wherein the administration is about once per week.

17. The method of claim 16, wherein the administration is about once per week with a dose of about 0.7 mg up to about 700 mg.

18. The method of claim 11, wherein the subject is undergoing antiretroviral therapy (ART).

19. The method of claim 18, wherein the antiretroviral therapy (ART) comprises an HIV protease inhibitor.

20. The method of claim 11, further comprising administering one or more additional therapeutic agents.

* * * * *

SEQUENCE LISTING

```
Sequence total quantity: 10
SEQ ID NO: 1            moltype = AA  length = 406
FEATURE                 Location/Qualifiers
source                  1..406
                        mol_type = protein
                        organism = Homo sapiens
SEQUENCE: 1
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGSD SSPLLQFGGQ  240
VRQRYLYTDD AQQTEAHLEI REDGTVGGAA DQSPESLLQL KALKPGVIQI LGVKTSRFLC  300
QRPDGALYGS LHFDPEACSF RELLLEDGYN VYQSEAHGLP LHLPGNKSPH RDPAPRGPAR  360
FLPLPGLPPA LPEPPGILAP QPPDVGSSDP LSMVGPSQGR SPSYAS                 406

SEQ ID NO: 2            moltype = AA  length = 419
FEATURE                 Location/Qualifiers
source                  1..419
```

-continued

```
                        mol_type = protein
                        organism = Homo sapiens
SEQUENCE: 2
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVGPS QGRSPSYAS   419

SEQ ID NO: 3            moltype = AA  length = 177
FEATURE                 Location/Qualifiers
source                  1..177
                        mol_type = protein
                        organism = Homo sapiens
SEQUENCE: 3
DSSPLLQFGG QVRQRYLYTD DAQETEAHLE IREDGTVGGA AHQSPESLLE LKALKPGVIQ  60
ILGVKTSRFL CQKPDGALYG SLHFDPEACS FRELLLEDGY NVYQSEAHGL PLHLPGNRSP  120
HCDPAPQGPA RFLPLPGLPP ALPEPPGILA PQPPDVGSSD PLAMVGPSQG RSPSYAS     177

SEQ ID NO: 4            moltype = AA  length = 406
FEATURE                 Location/Qualifiers
source                  1..406
                        mol_type = protein
                        organism = Homo sapiens
SEQUENCE: 4
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGSD SSPLLQFGGQ  240
VRQRYLYTDD ACQTEAHLEI REDGTVGGAA DQSPESLLQL KALKPGVIQI LGVKTSRFLC  300
QRPDGTLYGS LHFDPEACSF RELLLEDGYN VYQSEAHGLP LHLPCNRSPH RDPASRGPAR  360
FLPLPGLPPA LPEPPGILAP QPPDVGSSDP LAMVGGSQAR SPSYAS                 406

SEQ ID NO: 5            moltype = AA  length = 406
FEATURE                 Location/Qualifiers
source                  1..406
                        mol_type = protein
                        organism = Homo sapiens
SEQUENCE: 5
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGSD SSPLLQFGGQ  240
VRQRYLYTDD ACQTEAHLEI REDGTVGGAA DQSPESLLQL KALKPGVIQI LGVKTSRFLC  300
QKPDGALYGS LHFDPEACSF RELLLEDGYN VYQSEAHGLP LHLPCNRSPH RDPASRGPAR  360
FLPLPGLPPA LPEPPGILAP QPPDVGSSDP LAMVGGSQAR SPSYAS                 406

SEQ ID NO: 6            moltype = AA  length = 406
FEATURE                 Location/Qualifiers
source                  1..406
                        mol_type = protein
                        organism = Homo sapiens
SEQUENCE: 6
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGSD SSPLLQFGGQ  240
VRQRYLYTDD ACQTEAHLEI REDGTVGGAA HQSPESLLEL KALKPGVIQI LGVKTSRFLC  300
QKPDGALYGS LHFDPEACSF RELLLEDGYN VYQSEAHGLP LHLPCNRSPH RDPAPQGPAR  360
FLPLPGLPPA LPEPPGILAP QPPDVGSSDP LAMVGPSQGR SPSYAS                 406

SEQ ID NO: 7            moltype = AA  length = 419
FEATURE                 Location/Qualifiers
source                  1..419
                        mol_type = protein
                        organism = Homo sapiens
SEQUENCE: 7
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSDSSPLLQF GGQVRQRYLY TDDACQTEAH LEIREDGTVG GAAHQSPESL LELKALKPGV  300
IQILGVKTSR FLCQKPDGAL YGSLHFDPEA CSFRELLLED GYNVYQSEAH GLPLHLPCNR  360
SPHRDPAPQG PARFLPLPGL PPALPEPPGI LAPQPPDVGS SDPLAMVGPS QGRSPSYAS   419

SEQ ID NO: 8            moltype = AA  length = 419
FEATURE                 Location/Qualifiers
```

-continued

```
source                  1..419
                        mol_type = protein
                        organism = Homo sapiens
SEQUENCE: 8
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSDSSPLLQF GGQVRQRYLY TDDACQTEAH LEIREDGTVG GAADQSPESL LQLKALKPGV  300
IQILGVKTSR FLCQKPDGAL YGSLHFDPEA CSFRELLLED GYNVYQSEAH GLPLHLPCNR  360
SPHRDPASRG PARFLPLPGL PPALPEPPGI LAPQPPDVGS SDPLAMVGGS QARSPSYAS   419

SEQ ID NO: 9            moltype = AA  length = 419
FEATURE                 Location/Qualifiers
source                  1..419
                        mol_type = protein
                        organism = Homo sapiens
SEQUENCE: 9
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSDSSPLLQF GGQVRQRYLY TDDACQTEAH LEIREDGTVG GAADQSPESL LQLKALKPGV  300
IQILGVKTSR FLCQRPDGTL YGSLHFDPEA CSFRELLLED GYNVYQSEAH GLPLHLPCNR  360
SPHRDPASRG PARFLPLPGL PPALPEPPGI LAPQPPDVGS SDPLAMVGGS QARSPSYAS   419

SEQ ID NO: 10           moltype = AA  length = 15
FEATURE                 Location/Qualifiers
source                  1..15
                        mol_type = protein
                        organism = Homo sapiens
SEQUENCE: 10
GGGGSGGGGS GGGGS                                                   15
```